(12) United States Patent
Li

(10) Patent No.: US 8,000,903 B1
(45) Date of Patent: *Aug. 16, 2011

(54) COATED OR DOPED CARBON NANOTUBE NETWORK SENSORS AS AFFECTED BY ENVIRONMENTAL PARAMETERS

(75) Inventor: Jing Li, San Jose, CA (US)

(73) Assignee: The United States of America as represented by the Administrator of the National Aeronautics and Space Asministration (NASA), Washington, DC (US)

( * ) Notice: Subject to any disclaimer, the term of this patent is extended or adjusted under 35 U.S.C. 154(b) by 1050 days.

This patent is subject to a terminal disclaimer.

(21) Appl. No.: 11/416,505

(22) Filed: Apr. 28, 2006

Related U.S. Application Data

(63) Continuation-in-part of application No. 11/178,079, filed on Jul. 8, 2005.

(51) Int. Cl.
*G01N 31/00* (2006.01)

(52) U.S. Cl. ............... 702/22; 702/23; 702/24; 702/27; 702/30; 702/32; 422/83; 422/98; 436/149; 73/23.2; 73/23.21; 977/920; 977/921; 977/922; 977/938

(58) Field of Classification Search ............ 73/23.2, 73/23.21; 422/82.01–82.04, 83, 98; 436/150, 436/153; 204/547, 643; 702/22–24, 27, 702/32, 53; 706/45, 51
See application file for complete search history.

(56) References Cited

U.S. PATENT DOCUMENTS

| | | | |
|---|---|---|---|
| 6,289,328 B2 | 9/2001 | Shaffer | |
| 6,528,020 B1 * | 3/2003 | Dai et al. | ............ 422/98 |
| 6,537,498 B1 | 3/2003 | Lewis et al. | |
| 7,312,095 B1 | 12/2007 | Gabriel et al. | |
| 7,318,908 B1 | 1/2008 | Dai et al. | |
| 2003/0175161 A1 * | 9/2003 | Gabriel et al. | ............ 422/90 |
| 2005/0126913 A1 * | 6/2005 | Burke et al. | ............ 204/547 |
| 2005/0169798 A1 | 8/2005 | Bradley et al. | |

OTHER PUBLICATIONS

Shaffer et al., A comparison study of chemical sensor array pattern recognition algorithms, 1999, Elsevier Science B.V., Analytica Chimica Acta 384 (1999), p. 305-317.*

(Continued)

*Primary Examiner* — In Suk Bullock
*Assistant Examiner* — Robert Eom
(74) *Attorney, Agent, or Firm* — John F. Schipper; Robert M. Padilla

(57) ABSTRACT

Methods for using modified single wall carbon nanotubes ("SWCNTs") to detect presence and/or concentration of a gas component, such as a halogen (e.g., $Cl_2$), hydrogen halides (e.g., HCl), a hydrocarbon (e.g., $C_nH_{2n+2}$), an alcohol, an aldehyde or a ketone, to which an unmodified SWCNT is substantially non-reactive. In a first embodiment, a connected network of SWCNTs is coated with a selected polymer, such as chlorosulfonated polyethylene, hydroxypropyl cellulose, polystyrene and/or polyvinylalcohol, and change in an electrical parameter or response value (e.g., conductance, current, voltage difference or resistance) of the coated versus uncoated SWCNT networks is analyzed. In a second embodiment, the network is doped with a transition element, such as Pd, Pt, Rh, Ir, Ru, Os and/or Au, and change in an electrical parameter value is again analyzed. The parameter change value depends monotonically, not necessarily linearly, upon concentration of the gas component. Two general algorithms are presented for estimating concentration value(s), or upper or lower concentration bounds on such values, from measured differences of response values.

10 Claims, 22 Drawing Sheets

OTHER PUBLICATIONS

Clinke, et al., Pore structure of raw and purified HiPco single-walled carbon nanotubes, Chenical Physics Letters, 2002, 69-74, 365, www.elsevier.com/locate/cplett, Elsevier Science B. V.

Kong, et al., Nanotube Molecular Wires as Chemical Sensors, Science, Jan. 28, 2000, 622-655, 287, www.sciencemag.org/cgi/content/lful1/287/5453/622.

Li, The Cyranose Chemical Vapor Analyzer, Sensors, Aug. 2000, 1-9.

Li, Carbon Nanotube Applications: Chemical and Physical Sensors, Carbon Nanotubes: Science & Applications, 2004, 213-233, CRC Press LLC, Boca Raton, Florida.

Li, et al., Carbon Nanotube Sensors for Gas and Organic Vapor Detection, Nano Letters, 2003, 929-933, 3-7.

Li, et al., A Gas Sensor Array Using Carbon Nanotubes and Microfabrication Technology, Electrochemical and Solid-State Letters, 2005, H100-H102, 8, The Electrochemical Society, Inc.

Li, et al., Nano Chemical Sensors With Polymer-Coated Carbon Nanotubes, IEEE Sensors Journal, Oct. 5, 2006, 1047-1051, 6-5, IEEE.

Lu, et al., Room temperature methane detection using palladium loaded single-walled carbon nanotube sensors, Chemical Physics Letters, 2004, 344-348, 391, Elsevier B.V.

Lu, et al., A carbon nanotube sensor array for sensitive gas discrimination using principal component analysis, Journal of Electroanalytical Chemistry, 2006, 105-110, 593, Elsevier B.V.

Matthews, et al., Effects of Electrode Configuration on Polymer Carbon-Black Composite Chemical Vapor Sensor Performance, IEEE Sensors Journal, Jun. 2002, 160-168, 2-3, IEEE.

Young, et al., High-Sensitivity $NO_2$ Detection with Carbon Nanotube—Gold Nanoparticle Composite Films, Journal of Nanoscience and Nanotechnology, 2005, 1509-1513, 5, American Scientific Publishers, USA.

Calusdian, et al., Design and Testing of a Wireless Portable Carbon Nanotube-Based Chemical Sensor System, Sixth IEEE Conference on Nanotechnology, Jun. 17-20, 2006, 794-797.

Shaffer, et al., A comparison study of chemical sensor array pattern recognition algorithms, Analytica Chimica Acta 384, 1999, 305-317, Elsevier.

Janata, Principles of Chemical Sensors, 1989, pp. 175-239, Plenum Press, New York.

\* cited by examiner

COATED OR DOPED CARBON NANOTUBE NETWORK SENSORS AS AFFECTED BY ENVIRONMENTAL PARAMETERS

ORIGIN OF THE INVENTION

This invention is a Continuation-In-Part of U.S. Ser. No. 11/178,079, filed 8 Jul. 2005, and was made, in part or whole, by one or more employees of the U.S. government.

The U.S. government has the right to make, use and/or sell the invention described herein without payment of compensation, including but not limited to payment of royalties.

FIELD OF THE INVENTION

This invention relates to use of carbon nanotube networks as sensors of chemical substances.

BACKGROUND OF THE INVENTION

Chemical sensors have been developed for decades now to detect gases and vapors at various concentration levels for deployment in a wide range of industrial applications. The detection usually centers on a change of a particular property or status of the sensing material (such as temperature, electrical, optical characteristics, etc.) upon exposure to the chemical species of interest. The selection of sensing material itself has spanned across the periodic table with a range of inorganic, semiconducting elements and organic compounds either in bulk or in thin film form. Perhaps the most widely investigated class of sensors is the high temperature metal oxide sensor, due to its high sensitivity with tin oxide as an example of sensor material. The most common $SnO_2$ sensor platform is a chemiresistor wherein the transport characteristics of a conducting channel of tin oxide are modulated by the adsorption of chemical species at elevated temperatures ($T \geq 350°$ C.). Other types of sensors include electrochemical cells, conducting polymer sensors, surface acoustic wave sensors and catalytic bead sensors.

While commercial sensors based on some of the above approaches are available, research continues on new sensing materials and transducer platforms for improved performance. Desirable attributes of next generation sensors include high sensitivity, in the parts per million (ppm) to parts per billion (ppb) range, low power consumption, room temperature operation, rapid response time, high selectivity and long term stability. Sensors based on the emerging nanotechnology promise to provide improved performance on all of the above metrics compared to the current micro and macro sensors. Nanomaterials exhibit small size, light weight, very high surface to volume ratio, increased chemical reactivity compared to bulk materials, and mechanical stability so that a sensing material can be refreshed or regenerated many times. All these properties are ideal for developing extremely sensitive chemical sensors.

Among the numerous nanomaterials, carbon nanotubes (CNTs) have received significant attention due to their unique electronic and extraordinary mechanical properties. Single-wall carbon nanotubes (SWCNTs) have an enormous surface area, as high as about 1600 $m^2$/gm, which leads to an increased adsorptive capacity for gases and vapors. With all the atoms on the surface, SWCNTs are expected to exhibit a change in properties sensitively upon exposure to the environment. Indeed, electrical conductivity of SWCNTs has been shown to change reproducibly in the presence of gases such as $NO_2$ and $NH_3$. This revelation has resulted in the fabrication of SWCNT-based chemical sensors by several groups.

The principal platform for such sensors has been a nanotube field effect transistor ("CNT-FET") with a single SWCNT serving as the conducting channel. This platform faces some serious difficulties for commercialization. First, the CNT-FET requires semiconducting SWCNTs for its operation, and selective growth of metallic versus semiconducting nanotubes is not possible today. Second, if an in situ chemical vapor deposition ("CVD") process is used in the device fabrication sequence, it is hard to make a single SWCNT grow horizontally in order to bridge a given distance between the source and the drain. Alternatively, one is forced to 'pick and place' a semiconducting SWNT from bulk samples. Finally, the chemical sensor market is too cost sensitive to rely on complex steps involved in CNT-FET fabrication resulting in low sensor yield and poor reproducibility.

What is needed is an approach using suitably modified nanomaterials, such as SWCNTs, that can detect presence of certain gas components whose presence cannot be detected by any simple means. Preferably, the method should provide high sensitivity (detection of parts per million or parts per billion of the target gas), high selectivity, room temperature operation, low power consumption, high throughput and low cost. Preferably, the method(s) should extend to detection of other gas components with at most modest changes in the nanomaterial modification procedures. Preferably, this method should allow estimation of the effects of change of local temperature, change of local relative humidity and temporal drift (change of baseline and sensitivity with elapsed time).

SUMMARY OF THE INVENTION

These needs are met by the invention, which provides a chemical sensor or sensor array for detecting presence, at or near room temperature, of one or more of N target gas components or molecules ($N \geq 1$) in a gas mixture contained in a chamber, by any ambient being considered. The sensor contains a network of SWCNTs that is connected to a controllably variable voltage difference or current source. The chamber may be closed, isolated and static; or, preferably, may allow gas flow-through and thus not be wholly isolated from the external environment. Alternatively, the chamber may be part or all of the external environment.

In a first embodiment, the SWCNTs in the network are partly or wholly coated with a selected polymer, such as chlorosulfonated polyethylene, hydroxypropyl cellulose, polystyrene or polyvinylalcohol, and the target molecule may be a hydrocarbon $C_mH_n$, (e.g., $CH_4$ or $C_3H_7$ or $C_2H_2$), an alcohol $C_mH_n$OH, a ketone (e.g., $CH_3(CO)CH_3$) or an aldehyde (e.g., $C_2H_5(COH)$). An algorithm, applicable to any embodiment, provides an estimate of target molecule concentration.

In a second embodiment, the SWCNTs in the network are doped with a selected transition element, such as Pd, Pt, Rh, Ir, Ru, Os and/or Au. In either embodiment, a value of an electrical parameter, such as conductivity, resistivity, electrical current or voltage difference, is measured and compared with the parameter value for the network with no coating and no doping. SWCNTs are positioned between the electrodes using either a solution casting process in the form of a network or in situ growth using chemical vapor deposition (CVD) techniques. Polymer coating or transition element doping of SWCNTs allows selective sensing of certain gases, as demonstrated here for chlorine ($Cl_2$), HCl, $CH_4$ and $CO_x$ vapor. The CNT sensors may be formed on a substrate, such as silicon, ceramic, glass and selected polymers. The sensor fabrication process is scalable for manufacturing products that include wafer scale interdigitated electrode fabrication and inkjet deposition of SWCNTs and polymers for coatings and metal nanoparticles for doping. Coating and doping may be collectively referred to as "loading."

In a third embodiment, an array of substantially identical SWCNTs are (i) coated, as in the first embodiment, or (ii) doped, as in the second embodiment, a temperature gradient is imposed on the array, and a value of an electrical parameter is determined for each coating or doping tested, and a change in sensitivity is determined or estimated as a function of the local temperature value or gradient.

In a fourth embodiment, a sequence of substantially identical SWCNTs are (i) coated, as in the first embodiment, or (ii) doped, as in the second embodiment, different relative humidity values (e.g., 0, 15, 30, 50, 70 and 90 percent) or other environmental parameter values are imposed on each SWCNT sensor, a value of an electrical parameter is determined for each coating or doping tested, and a change in sensitivity is determined or estimated as a function of changes in the environmental parameter value.

In a fifth embodiment, an array of substantially identical SWCNTs are (i) coated, as in the first embodiment, or (ii) doped, as in the second embodiment, a value of an electrical parameter is determined for a selected local temperature and a selected local relative humidity, at the end of each of a sequence of selected time intervals, with temporal lengths from a few seconds to six months or more, if desired, and a change in baseline and sensitivity or "drift" is determined or estimated as a function of elapsed time. An algorithm is presented that can compensate for this drift in baseline and sensitivity, as a function of time.

BRIEF DESCRIPTION OF THE DRAWINGS

FIGS. 15-1 through 15-3 graphically present sequences of measurements of a response parameter W (electrical resistance) for an array of coated SWCNTs, as a function of $NO_2$ gas concentration for varying relative humidity values of 0, 30, 50, 70, 90 percent.

DESCRIPTION OF BEST MODES OF THE INVENTION

Figure 1:
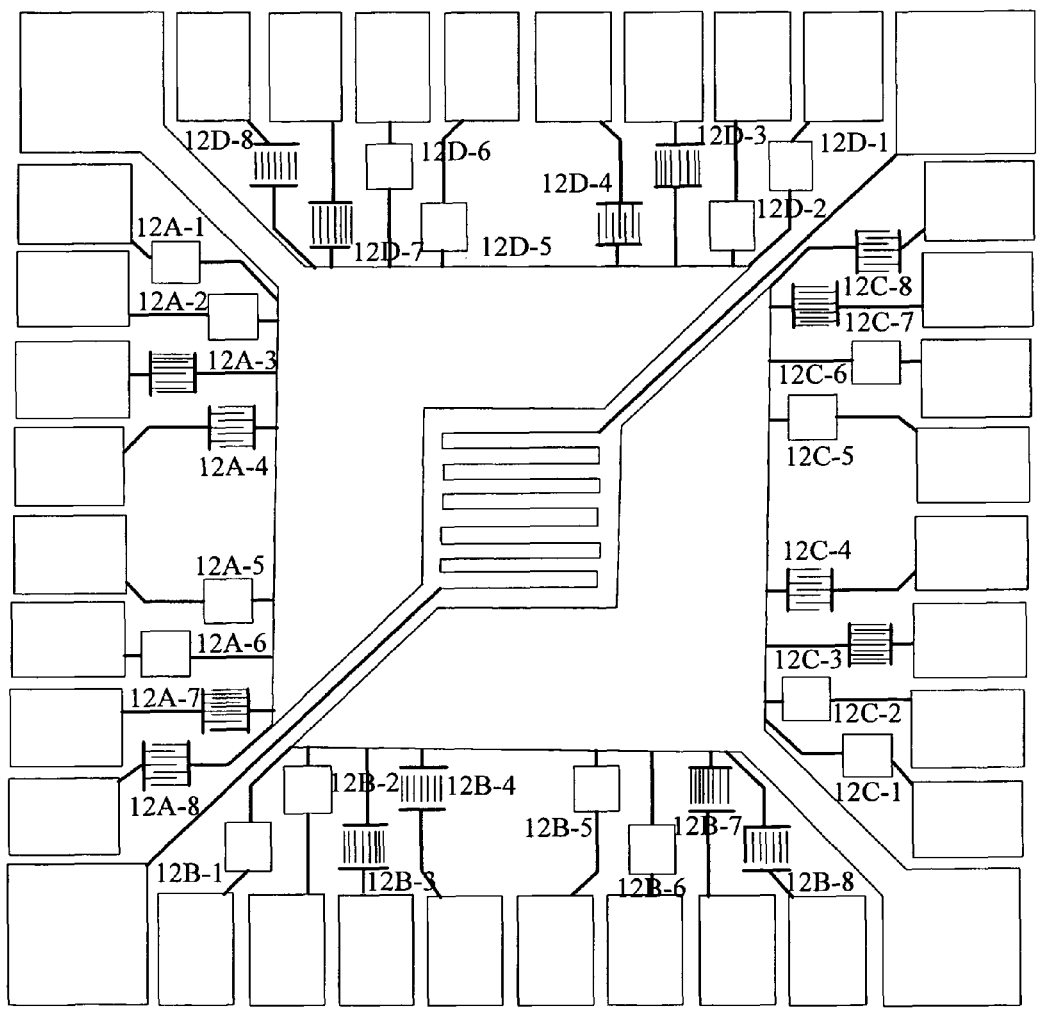
FIG. 1 illustrates use of an array of sensors, each using a network of SWCNTs to connect two electrodes according to the invention.

FIG. 1 illustrates a sensor 11, constructed according to an embodiment of the invention, including 32 interdigitated electrode fingers ("IDEFs"), 12A-1 through 12D-8, connected to first and second voltage sources, with a controllable voltage difference. In FIG. 1, a 1 cm×1 cm chip with Q sensing elements and SWCNTs bridging the gaps between adjacent IDEFs (Q=2-32). Each IDE was fabricated using conventional photolithography with a nominal finger width of 10 μm and gap sizes d=8, 12, 25 and 50 μm, or any other desired set of gap sizes. The fingers and contact pads were thermally evaporated Ti (20 nm thickness) and Pt (200 nm thickness) on a layer of $SiO_2$, thermally grown on a silicon substrate. The sensing material was bulk-produced SWCNTs from a HiPCo process (Rice University.), purified to remove amorphous carbon and metal impurities according to a procedure described in the literature. The purified SWCNTs were dispersed in a selected solvent, such as dimethyl formamide, to create a suspension of SWCNTs. The suspension was sonicated, then drop-deposited onto the interdigitated area of the electrodes. After the solvent evaporated, the SWCNTs formed a network connecting two adjacent IDEFs with a corresponding voltage difference. Any residue of the solvent was thoroughly removed by drying the sensor under vacuum. The SWCNT density in the network can be varied by varying the amount of suspension or the concentration of SWCNTs in the suspension placed on the sensor area. This process produces a statistically meaningful number of SWCNTs bridging the gap between two terminals to give reproducible performance. Alternatively, the SWCNTs can be grown directly on the electrodes using chemical vapor deposition. A selected electrical parameter response value, such as conductance or resistivity or electrical current or voltage difference, is provided or measured for the uncoated and coated SWCNT networks. Differences between the sensing elements are compensated for by varying a base resistance located in series with each sensing element.

SWCNTs yield different signal responses when exposed to different gases and vapors and one must use pattern recognition or intelligent signal processing techniques for the identification of the gas constituent of interest. SWCNTs do not respond to exposure to certain gases and vapors, and in those cases, coating or doping of the nanotubes may elicit a signal. Hydroxypropyl cellulose, having a mass of 0.791 gm, was dissolved in a solvent of 25 ml chloroform for coating the nanotubes to detect presence of HCl. In each case, an aliquot of 5 ml polymer solution was drop-deposited onto the SWCNT network in FIG. 1A to coat the corresponding SWCNTs.

In one version of the system shown in FIG. 1, eight of the IDEFs (12A-1 through 12A-8) are doped with mono-layer protected clusters ("MPCs") of Au, eight of the IDEFs (12B-1 through 12B-8) are coated with hydroxypropyl cellulose, and sixteen of the IDEFs (12C-1 through 12D-8) are "bare" CNTs. In another version, each IDEF, or subsets including more than one IDEF, is coated or doped with a (different) selected coating or dopant material so that the presence (or absence) of up to 31 or 32 different target materials can be tested.

The electrical current through the sensors, at a constant voltage of 1 Volt, was monitored as different concentrations of chemicals, such as chlorine ($Cl_2$) and of hydrochloric acid (HCl) vapor were sequentially introduced to the sensor's environment. A voltage difference of less than 1 Volt (or greater, if desired) can be used here. A computerized gas blending and dilution system, Environics 2040 (Environics, Inc. Tolland, Conn.), was used to create different concentration streams with a steady flow of 400 cc/min during both exposure and purge periods. A gas cylinder containing 98.3 ppm $Cl_2$ gas balanced with nitrogen, and a gas cylinder containing 478 ppm HCl with nitrogen, were used as the source gases. Nitrogen was used both as the purge gas and as the balance gas for creating low concentration test samples. The test sample concentrations were 1, 2 and 5 ppm for $Cl_2$ gas and 5, 10 and 40 ppm for HCl gas. The electrical signal (current) was collected using a semiconductor parameter analyzer HP4155B (Agilent, Palo Alto, Calif.). Other equivalent electrical parameters, such as conductance or resistance, can be used as a response value. In trials involving heating, a thermal controller, Micro-Infinity ICN77000 Series Controller (Newport Electronics, Inc., Santa Ana, Calif.) with a thermocouple, maintained a constant temperature for the sensor operation. Additionally, a vacuum pump and an ultraviolet lamp of wavelength 254 nm were employed on occasion to accelerate the recovery of the sensors between tests; other ultraviolet wavelengths, such as 300 nm and 360 nm, can also be used to accelerate recovery.

Carbon nanotubes do not sense presence of some gases and vapors due to the chemical and physical properties of CNTs as well as the nature of interaction between the gas molecules and nanotubes. SWCNTs have been found to detect presence of $NH_3$ and/or $NO_2$, based on the charge transfer between these gases and SWCNTs. Our early tests indicated that pristine SWNTs do not respond at all when exposed to some industrial chemicals, such as chlorine and hydrogen chloride. It is important to get some observable response before one can do signal processing or pattern recognition for selective identification.

Carbon nanotubes coated with different polymers, such as chlorosulfonated polyethylene, hydroxypropyl cellulose, polystyrene, polyvinylalcohol, etc. used in commercial polymer based chemical sensors available for organic vapor detection, can provide specific interactions with a chemical species of interest. As this chemical treatment aims to provide a specific interaction between the carbon nanotube matrix and specific gas molecules, the treatment can improve the selectivity while maintaining the high sensitivity expected of a nanosensor.

Figure 2:
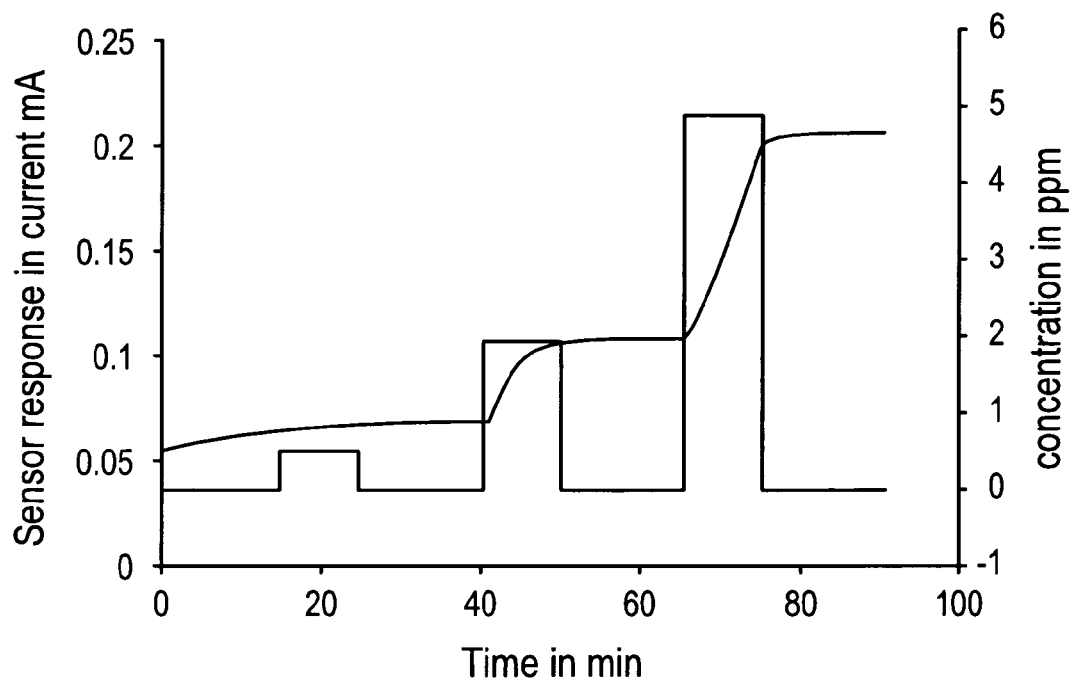
FIGS. 2 and 3 graphically illustrate sensor response (electrical current) versus concentration (C) for $Cl_2$ detection and for HCl detection, using SWCNTs coated with chlorosulfonated polyethylene and hydroxypropyl cellulose, respectively.

Several polymer-coated carbon nanotube sensors have been tested for different toxic gases, such as chlorine and hydrogen chloride; for comparison, other gases, including oxides of nitrogen ($NO_p$; p=1-3), ammonia ($NH_3$), benzene, nitrotoulene and acetone, have also been tested. FIG. 2 shows the room temperature sensor response for SWCNTs coated with chlorosulfonated polyethylene, for $Cl_2$ concentration pulses of 1, 2 and 5 ppm as shown by the sample pulses. At 1 ppm of $Cl_2$, no response is observed. but significant response is seen at 2 ppm and above. The signal strength increases at higher concentrations. Such concentration-dependent signal response is a desirable attribute. By contrast, many state of the art sensors provide a flat signal regardless of the concentration. The sensor results shown in FIG. 2 are consistently reproducible. However, the sensor recovery time is currently an issue, as is implicit in the times required ($\approx$10 min) for reaction to change of concentration. From our previous work with $NO_p$ sensing, it is known that UV illumination of the SWNTs helps to drive out the adsorbents rapidly, thus accelerating recovery when the source of the test sample is removed.

Figure 3:
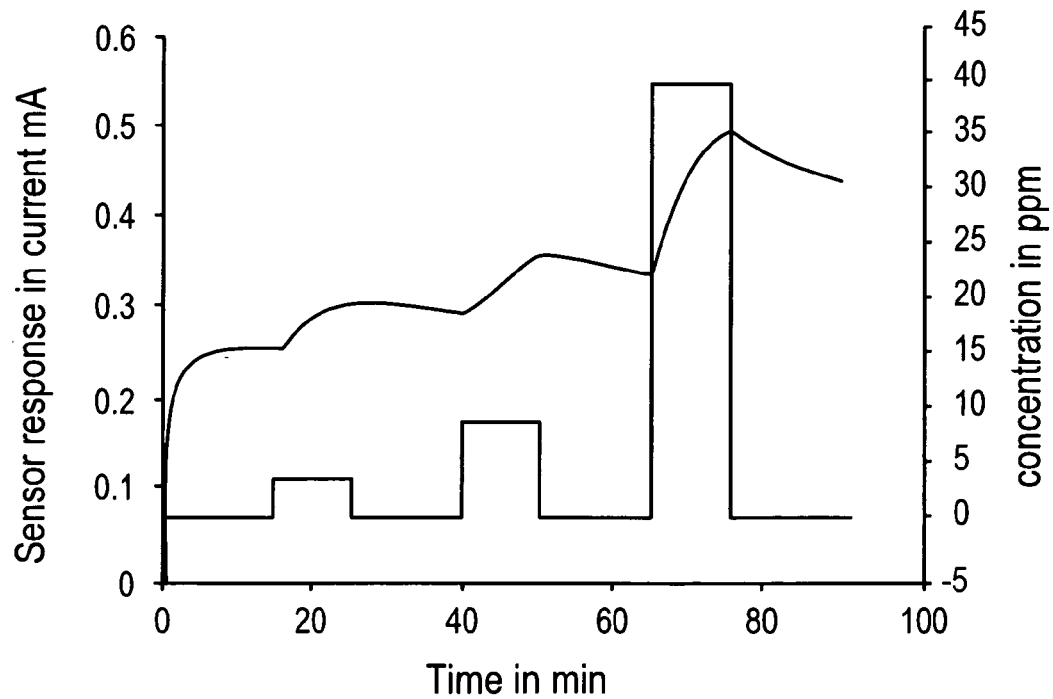

Sensors with SWCNTs coated with hydroxypropyl cellulose have been tested for HCl detection. FIG. 3 shows the sensor response, as a function of time, for HCl concentration pulses of 5, 10 and 40 ppm. This sensor provides an observable response signal with 5 ppm HCl present, with reasonable recovery times similar to those in FIG. 2. Again, the (equilibrium) signal increases with the concentration of the analyte, and the sensor results are highly reproducible. Although the response and recovery times of this sensor for HCl are improved relative to the results for chlorine, UV illumination and heating may be used here as well for further improved performance.

Figure 4:
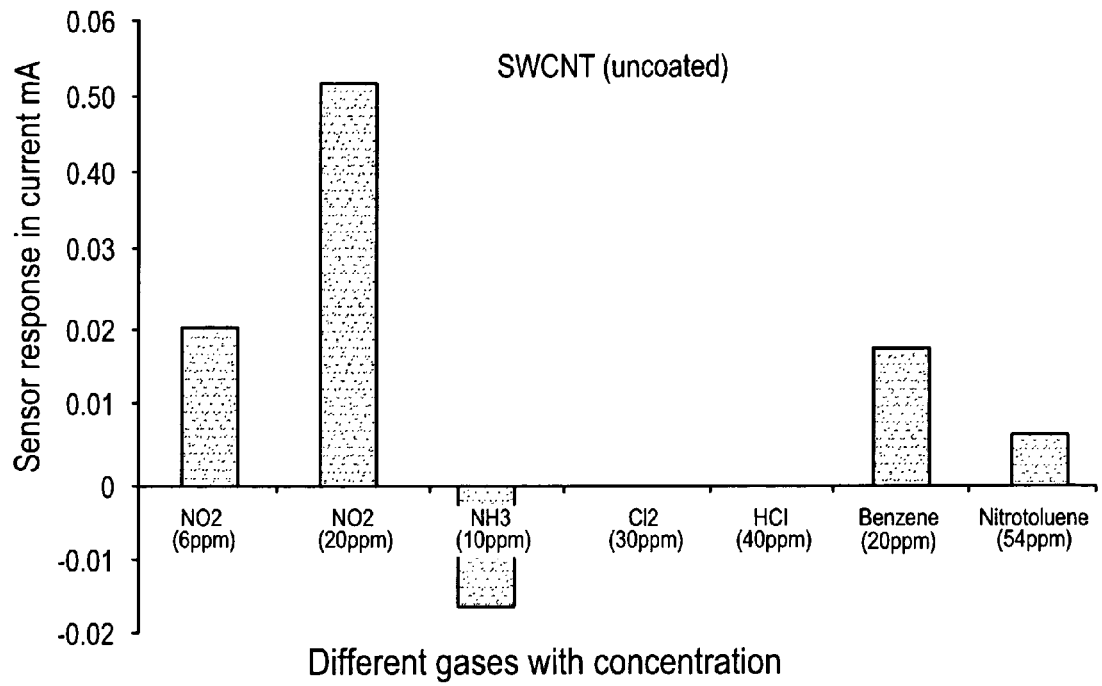
FIG. 4 compares relative response of uncoated SWCNTs for presence of $NO_2$, $NH_3$, benzene, nitrotoluene, $Cl_2$ and HCl.

A comparison experiment was conducted on sensors using pure, uncoated SWCNTs exposed to different gas and vapor analytes, with results shown in FIG. 4. The pure or uncoated SWCNT sensors showed no observable response when exposed to $Cl_2$ or to HCl, but displayed positive response signals, varying with concentration, for $NO_p$, nitrotoulene, and benzene, and showed a negative response signal (opposite polarity) for $NH_3$. Thus, the SWCNT sensor has some low level of discriminating power by itself to some, but not all, gases and vapors. It is clear from FIG. 4 that SWCNTs sensors are sensitive to $NO_p$, nitrotoluene, benzene and $NH_3$, as demonstrated previously. The opposite polarities of sensor response for $NO_p$ and for $NH_3$ is believed to be due to the electron-acceptance and electron-donation characteristics of these gases. In relative terms, SWCNT sensors have lower sensitivity to benzene and to nitrotoluene vapors than to $NO_p$.

Figure 5:
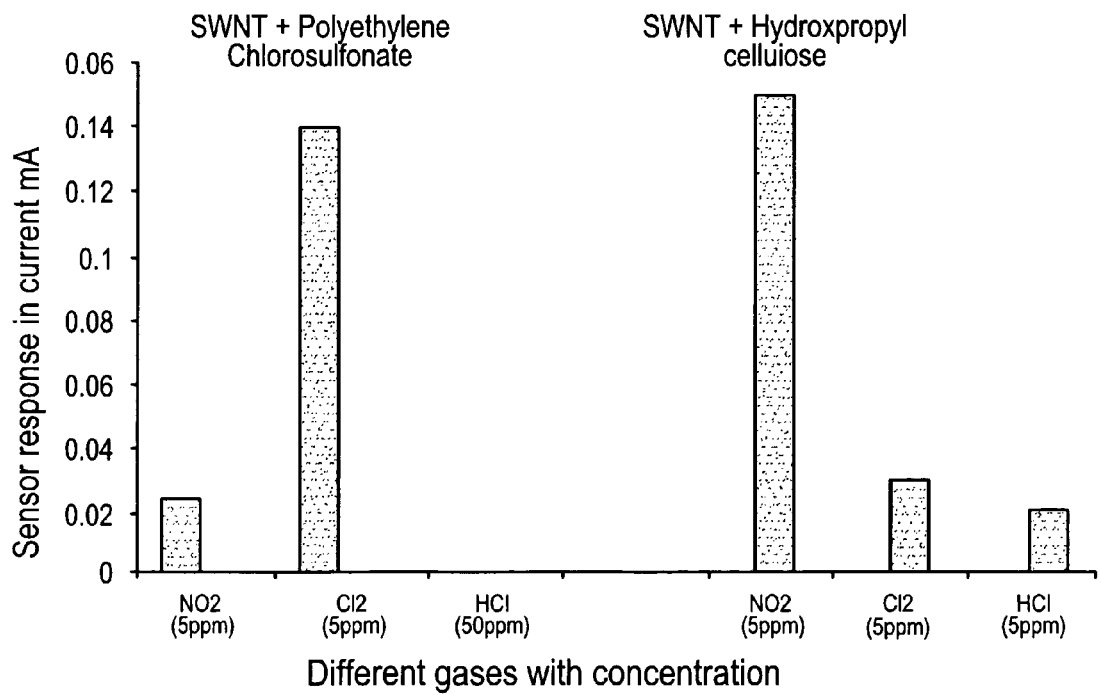
FIG. 5 compares relative response of SWCNTs coated with chlorosulfonated polyethylene or with hydroxypropyl cellulose for presence of $NO_2$, $Cl_2$ and HCl.

A similar comparison experiment was carried out on the polymer-coated SWCNT sensors exposed to different analytes, with results shown in FIG. 5. It is clear that addition of chlorosulfonated polyethylene coating to SWCNTs increases the sensitivity dramatically with a high level signal to 5 ppm $Cl_2$ compared to the pure SWCNT sensor, which shows no observable response even at 50 ppm of $Cl_2$ concentration. Although there is a signal for $NO_2$ from a chlorosulfonated polyethylene-coated SWCNT sensor, the sensing signal ratio of $Cl_2$ to $NO_2$ is much larger than 1. Therefore, this sensor can be used in a sensor array to give a distinct response signal for $Cl_2$ (and, similarly, for HCl) for discrimination.

These studies also show that both pure SWCNTs and chlorosulfonated polyethylene-coated SWCNTs do not respond to 100 ppm concentration of HCl gas in nitrogen. Higher concentrations of HCl were not tested as these high levels are not of interest for a nanosensor. In contrast, hydroxypropyl cellulose-coated SWCNTs respond to presence of HCl, but this sensor is also sensitive to $NO_2$. Presence of the OH groups in the polymer coating may be responsible for the response signal differences in interaction with acidic gases. Because this sensor gives a significant response to HCl that other SWCNT sensors do not, the sensor can be used in a sensor array to provide a chemical signature that differentiates the HCl gas from other chemicals.

We have demonstrated a simple nano-chemical sensor using polymer-coated SWCNTs as the sensing medium. Because pristine (uncoated or unmodified) nanotubes do not respond observably to some chemicals of interest, it is important to explore coating or doping techniques to promote observable responses so that a broad application coverage can be ensured. We have found that the polymer coating enables selective sensing of chlorine and hydrochloric acid vapor at a sensitivity level of 5 ppm and above. It is important to recognize that coating or doping alone is unlikely to provide absolute discrimination. As with most sensors (of any size or exploiting any property change), pattern recognition techniques would be a valuable and necessary complement to provide discrimination. In that regard, the use of sensor arrays with multiple elements is an effective approach to chemical sensing, wherein the data from multiple sensors can be routed to a signal processing chip, integrated into the system, for data fusion and analysis. Advanced signal processing and pattern recognition techniques can be used to confirm (or refute) the assumed presence of a given species; in addition to the help from the selective coatings. Multiple sensing element arrays offer additional operational freedom when sensor recovery is slow and is a rate limiting process. Under such circumstances, a sensor would always be available while other sensors are in recovery mode.

Figure 6:
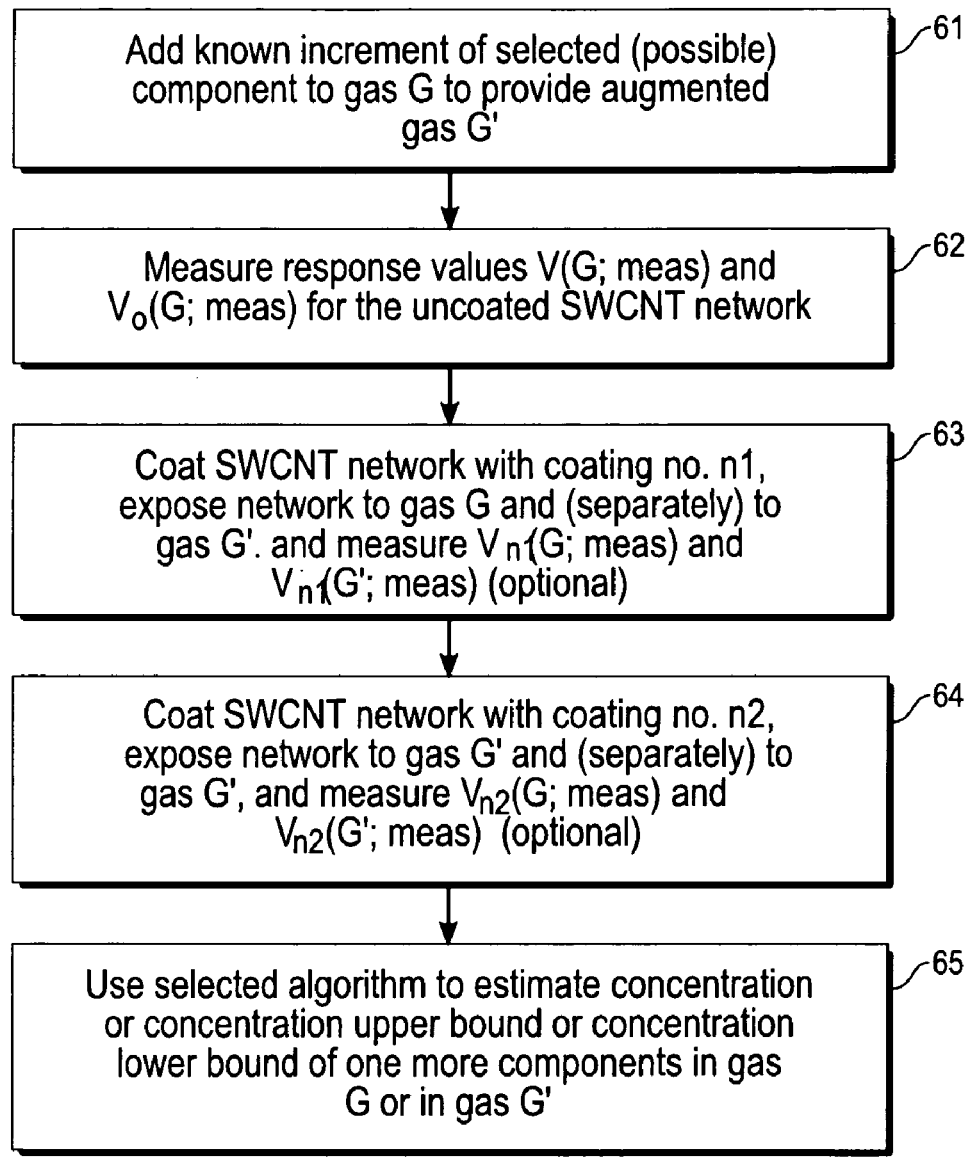
FIG. 6 is a flow chart for practicing the invention using one or more selected coatings (e.g., chlorosulfonated polyethylene or hydroxypropyl cellulose).

Using the results shown in FIG. 5, a procedure, shown as a flow chart in FIG. 6, can be implemented to detect presence of one, two or more target molecules, such as halogens, $F_2$ and/or $Cl_2$, or of one or more hydrogenated halogens, such as HF, HCl or HBr, in an unknown gas G (which may contain $NO_2$, $NH_3$ and one or more of the target gas molecules). In step 61, a known increment of a selected (possible) component of the gas G (reference component, such as $NO_2$ or $NH_3$, or target component, such as $Cl_2$ or HCl) is added to and mixed with a portion of the gas G to provide an augmented gas G'. In step 62, response values, $V_0(G;meas)$ and $V_0(G';meas)$, are measured for the uncoated SWCNT sensor In step 63, the SWCNT network is coated with a selected coating no. n1 (e.g., chlorosulfonated polyethylene, hydroxypropyl, polystyrene, polyvinylalcohol or another suitable (first) coating), is exposed to the gas G and (separately) to the gas G', and the corresponding response values $V_{n1}(G;meas)$ and $V_{n1}(G';meas)$ are measured or otherwise provided. In step 64, the SWCNT sensor is coated (instead) with a different selected coating no. n2 (e.g., hydroxypropyl cellulose or another suitable (second) coating), is exposed to the gas G and (separately) to the gas G', and the corresponding response values, $V_{n2}(G;meas)$ and $V_{n2}(G';meas)$ are measured or otherwise provided. In step 65, the system uses a selected algorithm to estimate the concentration (e.g., in ppb) or concentration upper bound or concentration lower bound of one or more of the components believed to be present in the gas G (or in the gas G'). Two suitable algorithms for determination of gas component concentration are disclosed in flow charts in FIGS. 7 and 8, discussed in Appendices A and B, respectively.

It is assumed initially in Appendix A that (i) the response value difference varies linearly with concentration difference of a single constituent that is present and (ii) the response value difference, in the presence of two or more gas constituents in the gas G, is the sum of the response value differences of the single constituent gases. Linear response coefficients $a_{ij}$ for the response value differences are assumed to be determined experimentally or otherwise provided. As an example, assume that one reference gas (e.g., $NO_2$ or $NH_3$) plus first and second target gases (e.g., $Cl_2$ and HCl), are suspected to be present in the gas G. Estimates of each of the concentration values $c_{m0}$ for the initial (unaugmented) gas G are obtained from inversion of an M×M matrix equation relating these concentration values to response value differences for N coatings, where M ($\geq 2$) is the number of gas components (reference and target) believed to be present and N ($\geq 1$) is the number of coatings (or dopings) used for the measurements.

The approach discussed in Appendix A allows separate weights, $w_n$ and $w'_n$ (or the same weight), to be assigned to the measurements of the initial gas and augmented gas. Preferably, at least two of the weight values in Eq. (3) are positive (e.g., $(w_1, w_2)$ or $(w'_1, w'_2)$ or $(w_1, w'_1)$ or $(w'_1, w_2)$) for the example with N=2, and the relative sizes of the non-zero weights reflect the relative importance of the response measurements. If, as is likely, the four response measurements are believed to be equally important, one can choose $w_1=w_2=w'_1=w'_2=1$. One can ignore one or two of the four measurements, in which event the corresponding weight value(s) is set equal to 0.

The response coefficients $a_{ij}$ used in Eqs. (1) and (2) are not necessarily positive. For example, the response coefficient $a_{ij}$ for the gas constituent $NO_2$ is positive for several of the SWCNT coatings used, while the response coefficient $a_{ij}$ for $NH_3$ is observed to be negative for some of these coatings.

Figure 8:
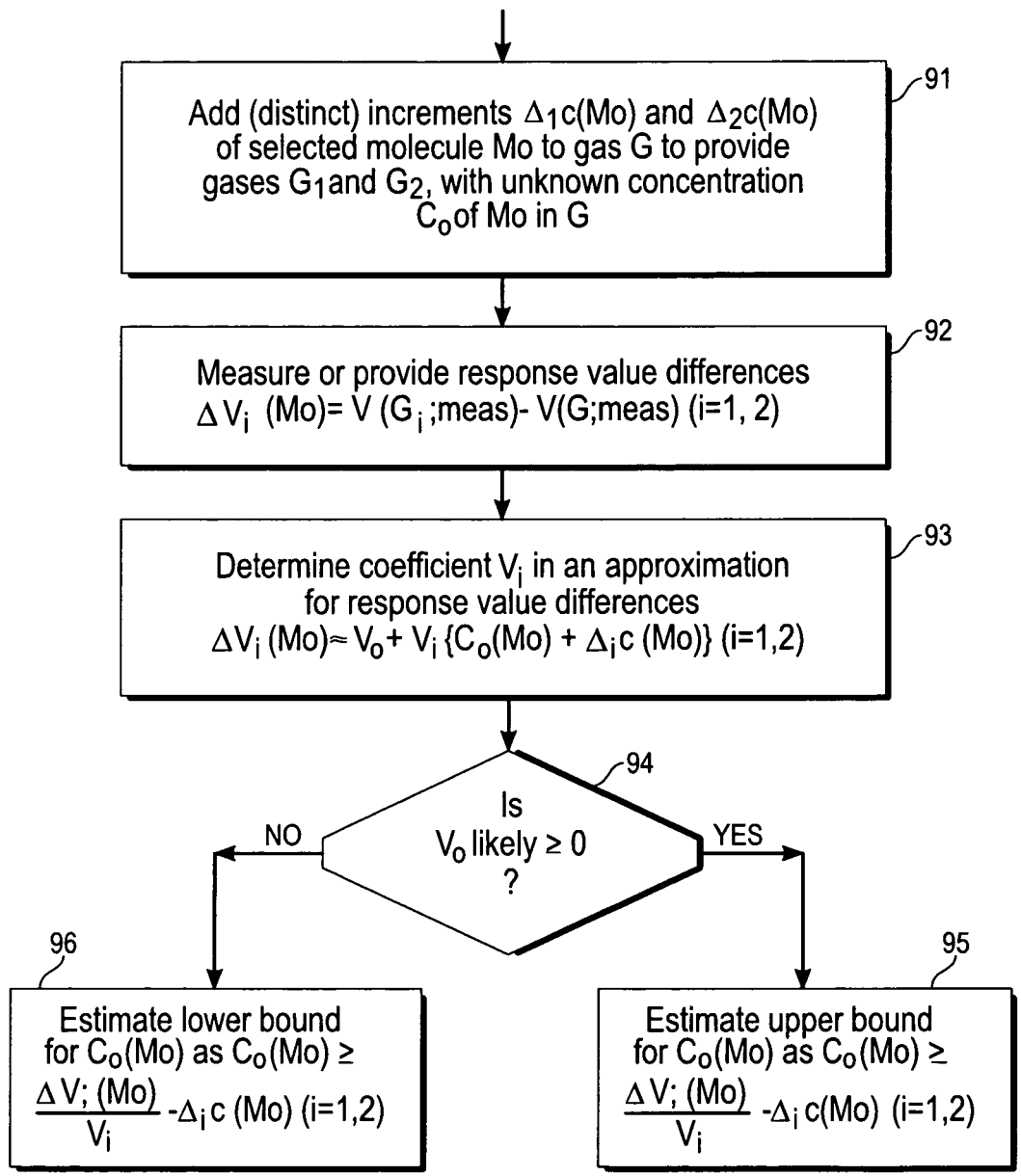

Appendix B, and the corresponding flow chart in FIG. 8, discuss an approach for estimating an upper bound, or a lower bound, of a concentration value of a selected molecule (e.g., $NO_x$ or $NH_3$ or $Cl_2$ or HCl), again assuming that a response value difference varies linearly with a concentration value difference of the selected molecule. This bound is computed separately for each selected molecule. Appendices A and B apply to coated or doped CNT networks.

Figure 9:
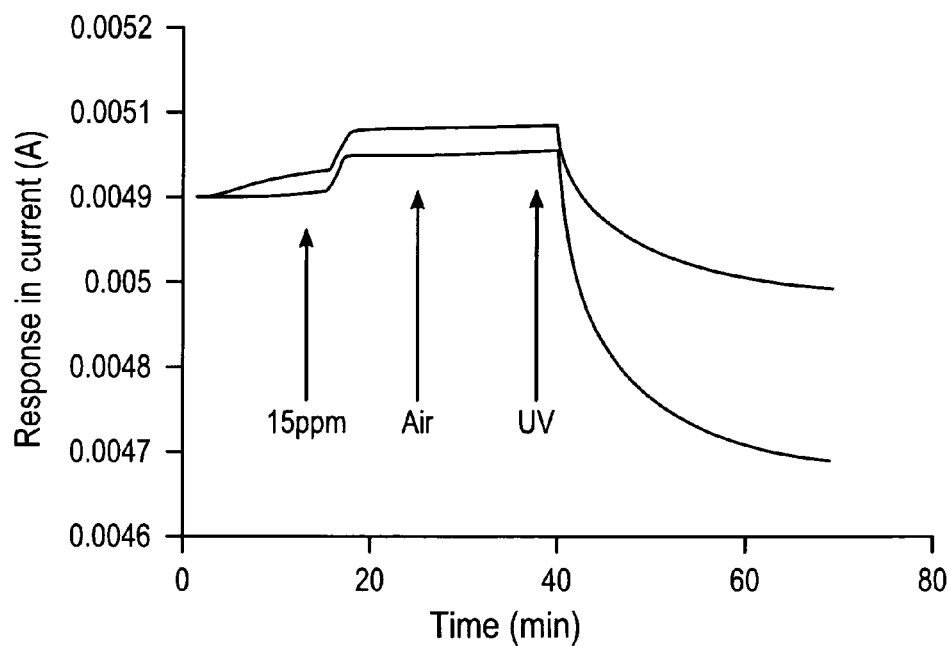
FIG. 9 graphically illustrates recovery time of a measured electrical parameter (here, current) to presence of ultraviolet light.

Exposure of the coated SWCNT network to ultraviolet light can reduce the recovery time (normally ten hours or more) required to return the network to a substantially uncoated condition, by promoting accelerated detachment of the coating material from the SWCNT network. FIG. 9 graphically illustrates measured response versus time with exposure to ultraviolet light for two different amounts of the same coating (sensors 1 and 2), indicating the improvement in recovery time where ultraviolet light is applied to lower the energy barrier to desorption of the adsorbed gas from the SWCNT network. The chemical and environmental time histories may cause the response curves to differ (FIG. 9).

For some relatively small molecules, such as methane ($CH_4$), other hydrocarbons, and oxides of carbon ($CO_x$; x=1, 2), an SWCNT network, doped with a transition element ("TE",) such as Pd, Pt, Rh, Ir, Ru, Os and Au, can be used to detect presence of these molecules by detecting a change in an electrical parameter (conductance, resistance, current or voltage difference) or response value associated with a path defined by an SWCNT network that extends between two electrodes having a controllable voltage difference or current. Some molecules, including nitrotoluene and phenol, are relatively strong electron donors and/or electron acceptors, and these molecules' presence can be readily detected using "bare" or unmodified SWCNTs. Other molecules, including but not limited to methane, hydrocarbons and carbon oxides, manifest little or no electron donor or electron acceptor action so that monitoring an electric parameter value V of an unmodified or "bare" SWCNT network will, by itself, not indicate presence or absence of these molecules.

Where $CH_4$ is adsorbed in a SWCNT/Pd matrix, the combination forms a weakly bound complex, such as $Pd^\delta(CH_4)^{-\delta}$, where δ is a relatively small positive number that need not be an integer. Methane, hydrocarbons and carbon oxides are "greenhouse" gases and require detection capabilities in the ppb—ppm range to have much utility in environmental monitoring. The sensing platform is similar to that illustrated in FIG. 1, where the SWCNT/TE compound serves as a current or voltage modifier whose electrical parameter value V changes when molecules of a selected target chemical, such as $CH_4$ or $C_mH_n$ or $CO_x$, are adsorbed on the SWCNT/TE compound, and the magnitude of the value V is monotonically increasing (not necessarily linearly) with increase in the amount of the target chemical present. This approach for detecting presence of a target molecule is often at least one order of magnitude more sensitive at room temperature than is detection using catalytic beads or metal oxides, in part due to (1) nanoscale-induced charge transfer between TE-loaded nanotubes and $CH_4$ molecules and (2) a relatively large surface area per unit volume for SWCNTs, which permits enhanced adsorption of hydrocarbon molecules (e.g., $CH_4$ and $C_mH_n$).

Fabrication of a sensing platform for the SWCNT/TE network begins with sputter coating of about 10 nm thick Pd onto a pile of SWCNT powder. The TE-loaded or TE-doped SWCNTs are then dispersed into distilled, deionized water (e.g., 0.1 mg of SWCNT/Pd in 10 ml of the water). This solution is then sonicated and drop deposited onto interdigitated electrode fingers to create an electrical sensor with an initial resistance in a range of about 0.2-1 kilo-Ohm. Current through the network, with a 1 Volt difference, was monitored where 6, 15, 30 and 100 ppm of $CH_4$ was present, using a gas stream flow of about 400 cc/min during exposure and during purge. Apart from preparation of the doped or loaded SWCNT network (as distinguished from coating a SWCNT network), the procedure for estimation of constituents present in a gas using a doped SWCNT network, is parallel to the procedure using a coated SWCNT network set forth in the FIG. 6 flow chart.

Vacuum pumping and exposure of the network to ultraviolet light ($\delta$=254 nm) are used to reduce the recovery time of the SWCNT/Pd (i.e., removal of the $CH_4$) between tests (no recovery if these recovery acceleration procedures are not implemented). FIG. 9 graphically illustrates measured response versus time with ultraviolet light present, indicating the improvement in recovery time where ultraviolet light is applied to lower the energy barrier to desorption of $CH_4$ molecules from the SWCNT/Pd network.

Figure 10:
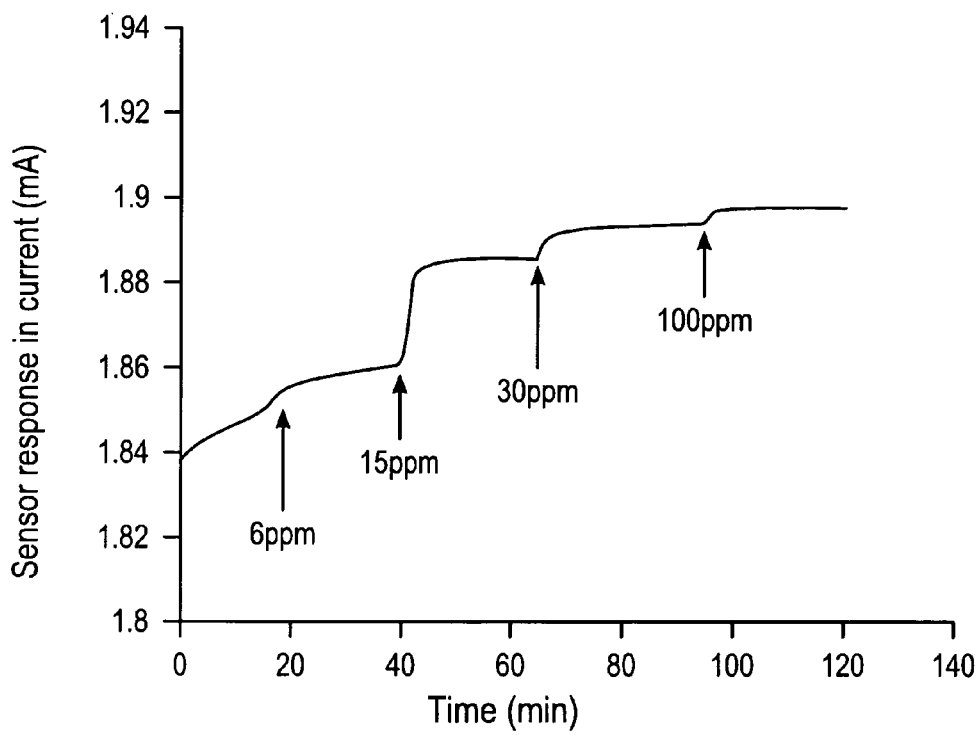
FIG. 10 graphically illustrates variation of a measured electrical parameter with time for different concentrations.

FIG. 10 graphically illustrates sensor response (current in milli-Amps) versus time for each of the $CH_4$ concentrations of 6, 20, 60 and 100 ppm, and also graphically illustrates fitting of a logarithmic function, $$V/V_0 \approx a \ln(C) - b = \ln\{C^a / \exp(b)\}, \quad (1)$$

to relative response $V/V_0$ versus $CH_4$ concentration c, for different sensor networks. Resistance, as the electrical parameter, normally decreases with increasing concentration C of the constituent, while conductance, electrical current and voltage difference normally increase with increasing concentration c. The algorithm set forth in Appendix 1 and illustrated in Eqs. (A3)-(A6) can be applied to estimate concentration of one or more of the gases $CH_4$, $C_mH_n$ and/or $CO_x$, by replacing the concentration $C_1$ or $C_2$ or $C_3$=C by the quantity $$x = \ln\{C^a / \exp(b)\}, \quad (2)$$

where the parameters a and b will vary with the particular gas constituent of interest.

Methane, in the presence of the SWCNT network, may form a complex such as $H[Pd] \cdot CH_3$. The H atoms in $CH_4$ tend to attract electrons from Pd, which in turn can obtain electrons from the SWCNTs to facilitate formation of the complex. This behavior should also be manifest for some or all of similar transition metals, such as Pt, Ru, Rh, Ir, Os and Au. The detection lower limit for $CH_4$ at room temperature, using a Pd-doped SWCNT network, is estimated to be a few hundred ppb to a few ppm. This compares with a $CH_4$ detection lower limit Of 0.5-1 percent for conventional sensors, at temperatures T(min)$\geq$450° C.

Figure 11:
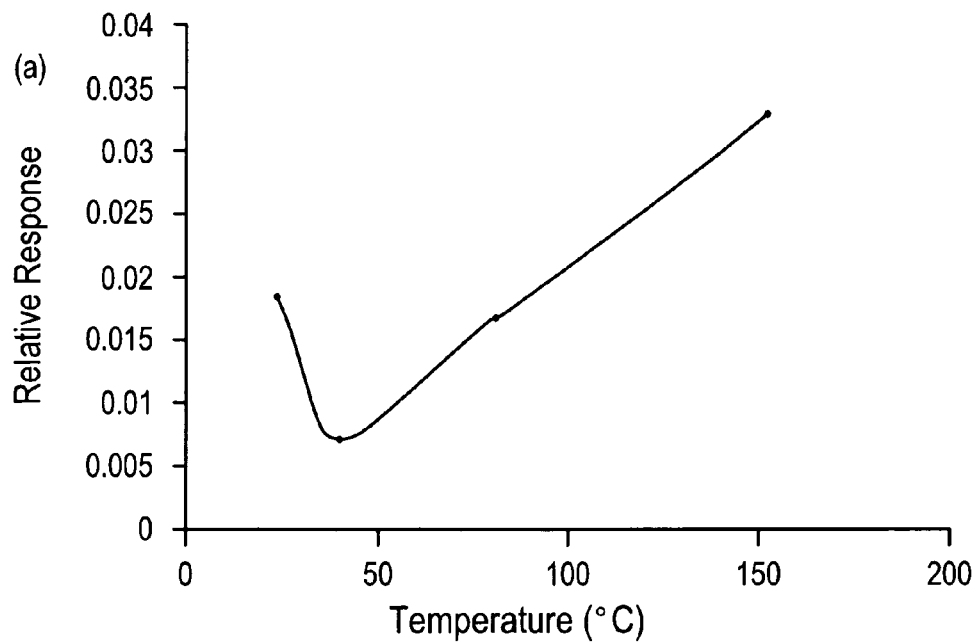
*FIGS. 11 and 12 graphically illustrate behavior of a measured electrical parameter and response time with varying temperature T.
Figure 12:
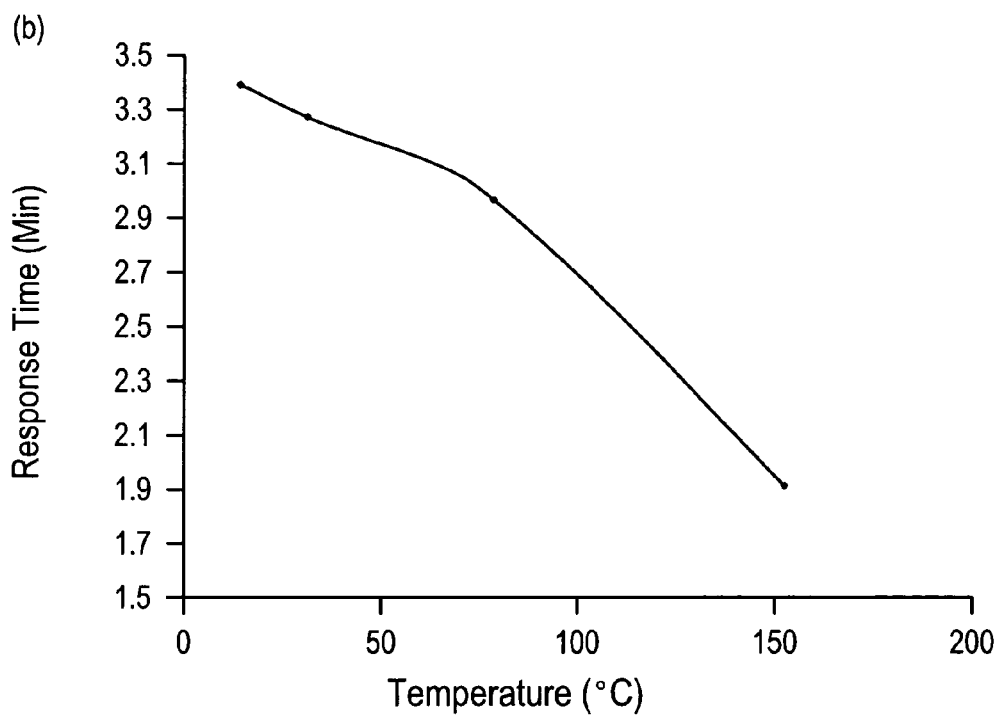

FIGS. 11 and 12 graphically illustrate the environmental effects of varying temperature upon relative response $V/V_0$ and upon response time, respectively, for SWCNTs plus Pd. The relative response in FIG. 11 appears to reach a relative minimum at a temperature T=T(min)$\approx$40° C. and to increase monotonically as |T −T(min)| increases. At room temperature, T$\approx$20° C., the relative response is approximately three times the relative response at T=T(min). The response time (required for approximate equilibration of the response after exposure to a gas containing the target molecule) decreases monotonically with increasing temperature T and increases with the amount of load (coating or dopant) used to treat the SWCNT The SWCNT/TE sensor, with TE=Pd, has been tested at 15 ppm and 30 ppm concentrations of $CH_4$ at gas temperatures of T=40° C., 80° C. and 150° C. The response parameter value (e.g., conductance or current) increases with increasing temperature, perhaps due to an enhanced catalytic effect of SWCNT/Pd binding with increasing temperature.

Experimental results for other hydrocarbons, for $CO_x$, for ketones and for aldehydes are qualitatively similar to those for $CH_4$.

Figure 13:
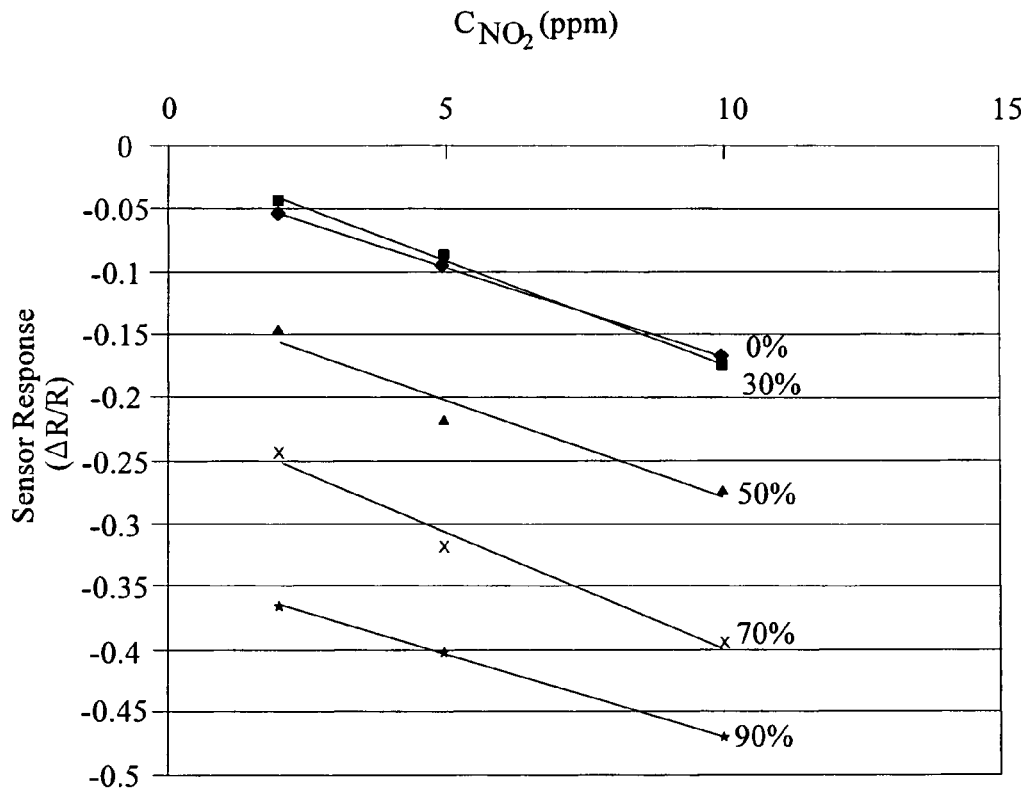
*FIG. 13 graphically illustrates behavior of a measured electrical parameter with varying relative humidity RH, for a SWCNT coated with hydroxypropyl cellulose.
Figure 14:
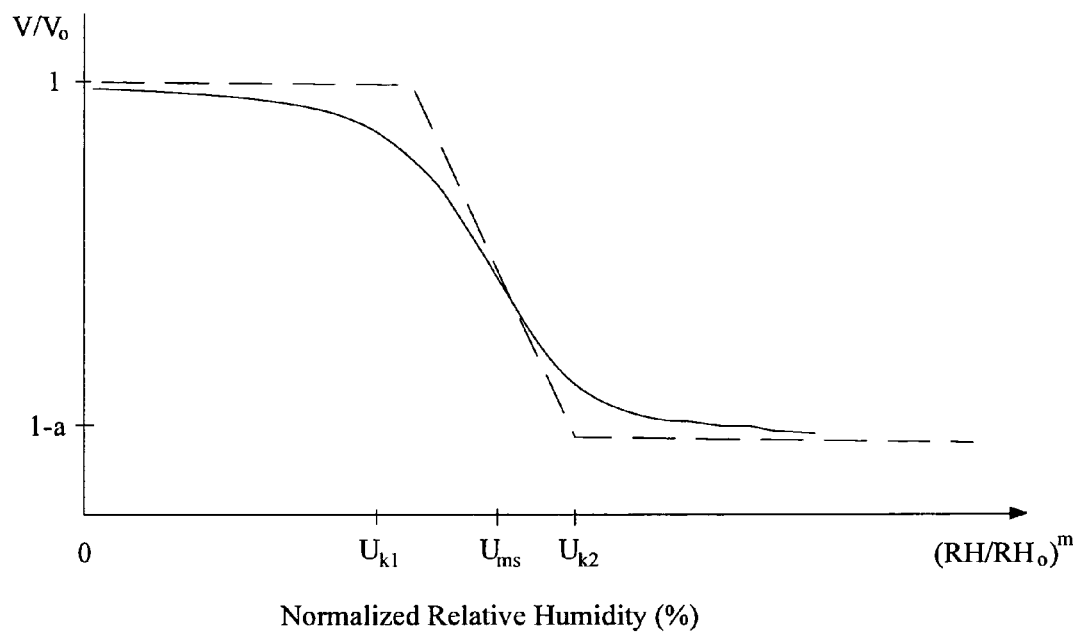
*FIG. 14 graphically illustrates variation of an approximation function for a measured electrical parameter with varying relative humidity RH for an SWCNT coated with an unspecified substance.

Effects of varying relative humidity (RH) on relative response, referenced to the response ($V_0$) at RH=0 percent, have been measured for several coating materials and doping materials, for a sequence of RH values. It is expected that relative response $V/V_0$ will decrease monotonically as the RH value increases, in part because the presence of a polar substance such as water would interfere with, and partly mask, the change $\Delta W$ in an electrical parameter, for substantially all coating and dopant materials of interest. This expectation is borne out in measurements of $V/V_0$, at $T=T_0$=40° C., presented graphically in FIG. 13, for the coating material hydroxypropyl cellulose, applied to a SWCNT, for RH=0, 15, 30, 50, 70 and 90 percent. Each of these curves for $V/V_0$ can be approximated or estimated by a parametrized curve such as $$V/V_0(RH;T_0) = F_e((RH/RH_0)^m; a) \approx a \cdot \text{sech}\{(RH/RH_0)^m\} + (1-a) \quad (3).$$

where $RH_0$ is a reference RH value, m is a positive number and 0<a$\leq$1, each value being chosen for the particular coating material or dopant material of interest. For sufficiently small values of the quantity $RH/RH_0$, the parametrized curve in Eq. (3) is further approximated as $$V/V_0(RH; T_0) \approx \quad (4)$$
$$a\{1 - (RH/RH_0)^{2m}/2\} + (1-a), = 1 - (a/2)(RH/RH_0)^{2m},$$

which is linear and decreasing in the quantity $(RH/RH_0)^{2m}$, and thus linear in the variable RH if 2m=1. More generally, the measured relative response value $V/V_0$ $(RH;T_0)$ is substantially monotonically decreasing in the value RH and resembles a trapezoid with a non-zero tail value, as illustrated in the generalized curve shown in FIG. 14.

Figures 1, 15:
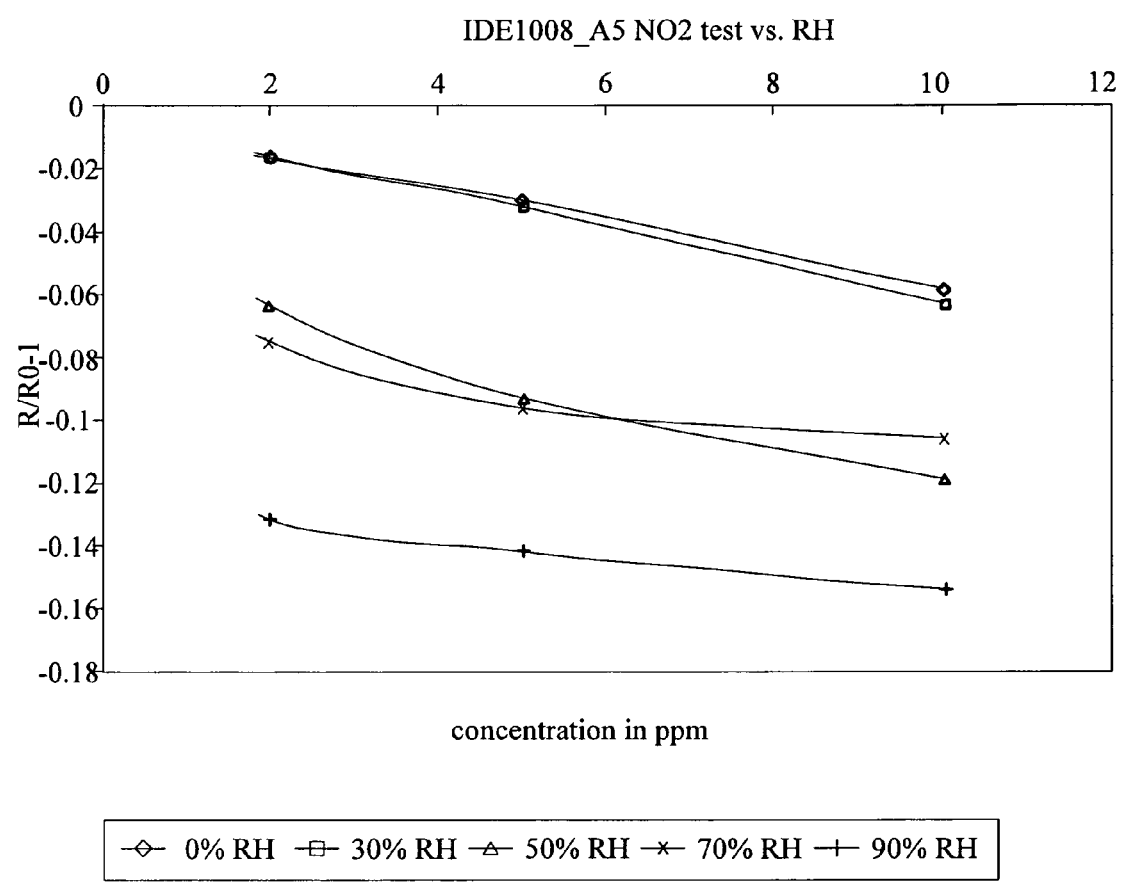
Figures 2, 15:
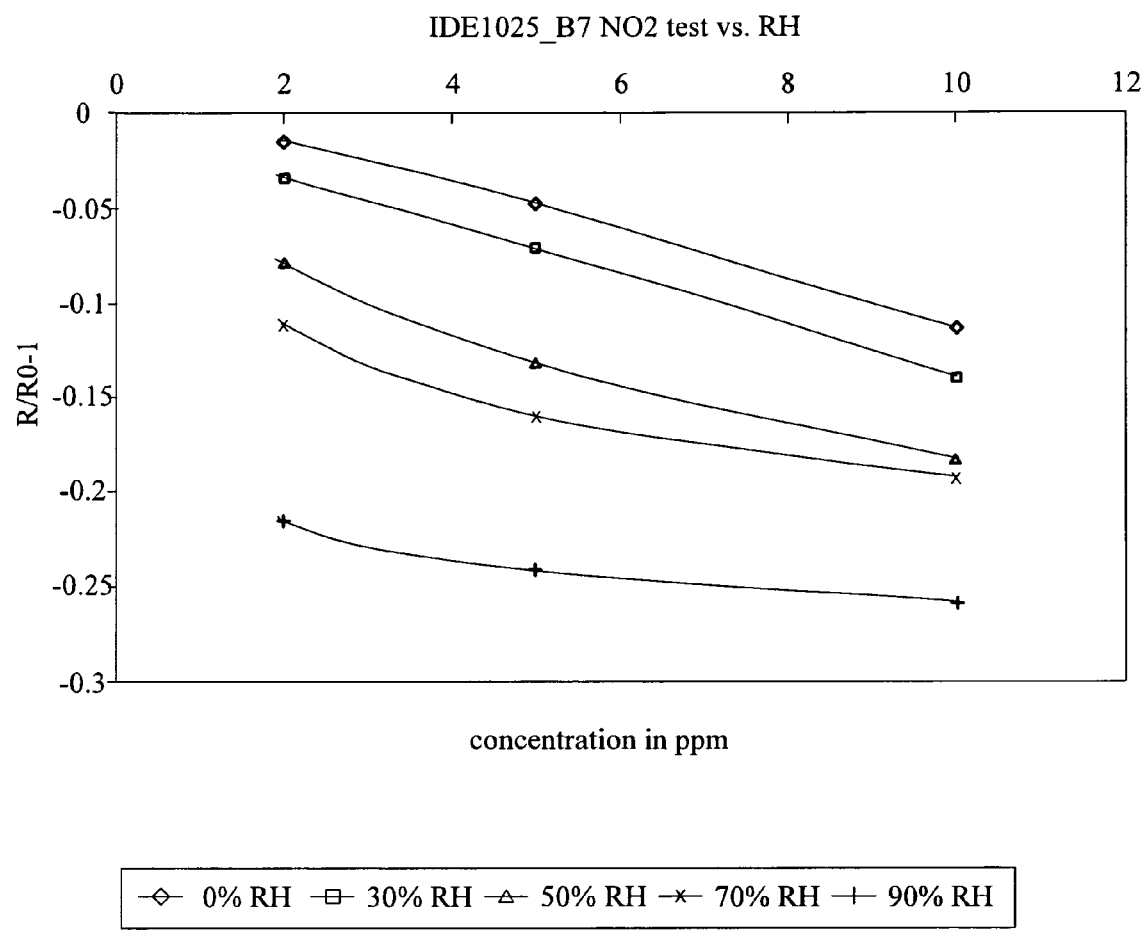
Figures 3, 15:
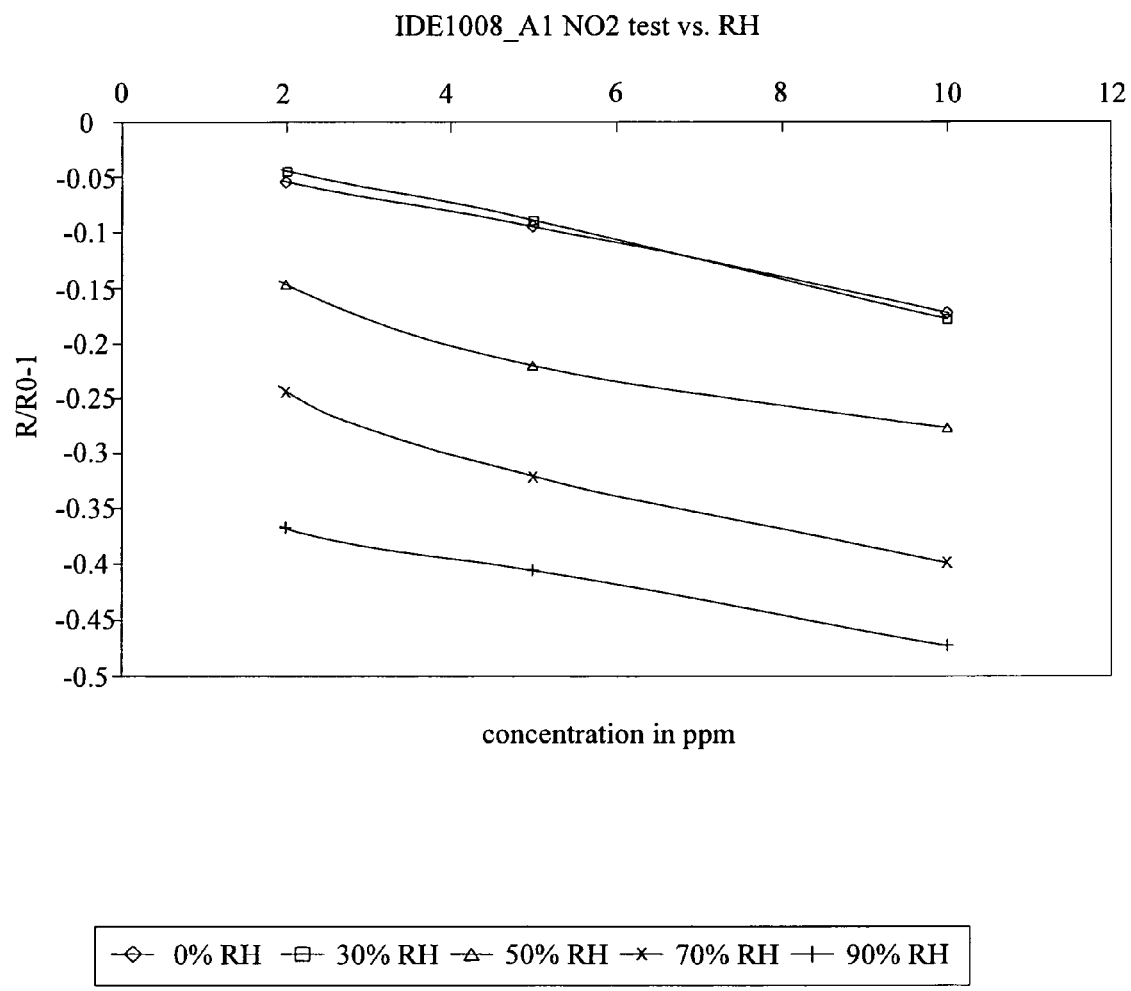
Figure 16A:
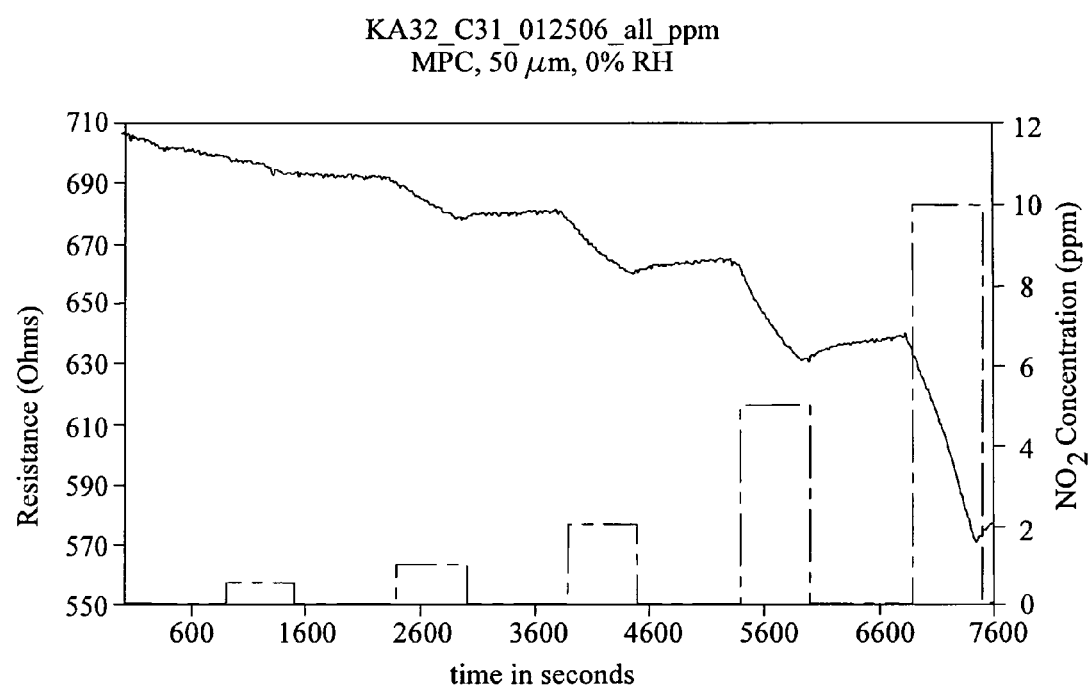
FIGS. 16A-16F graphically present measured values of a parameter W (electrical resistance) for a coated SWCNT, for varying relative humidity values RH and for time varying concentration values of $NO_2$ gas.
Figure 16B:
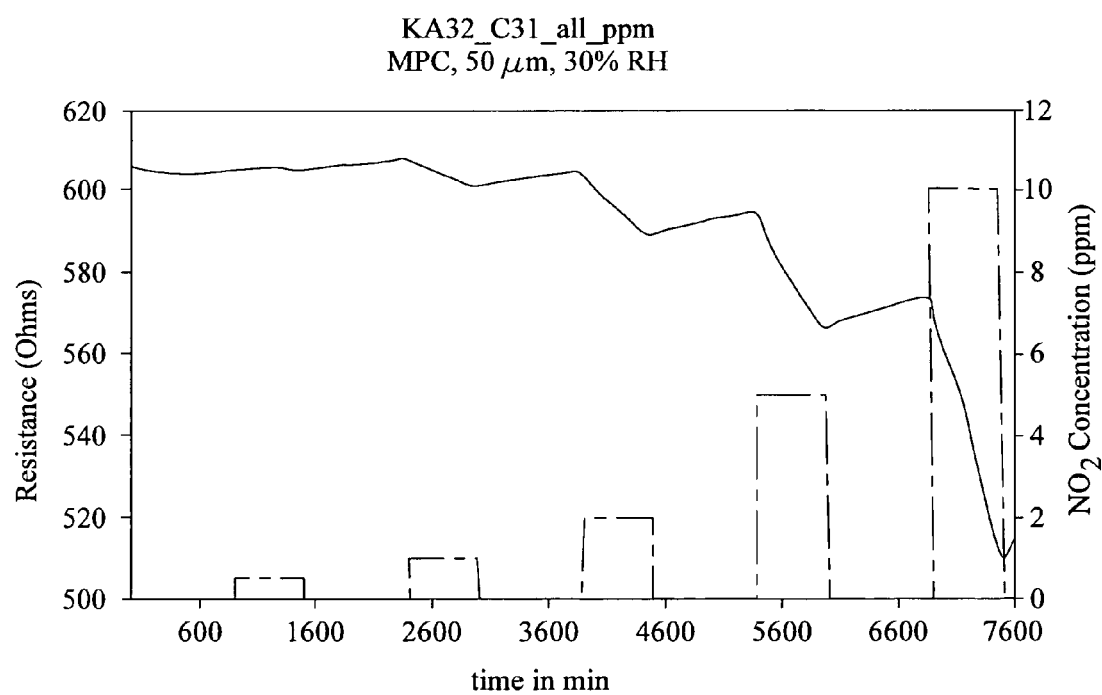
Figure 16C:
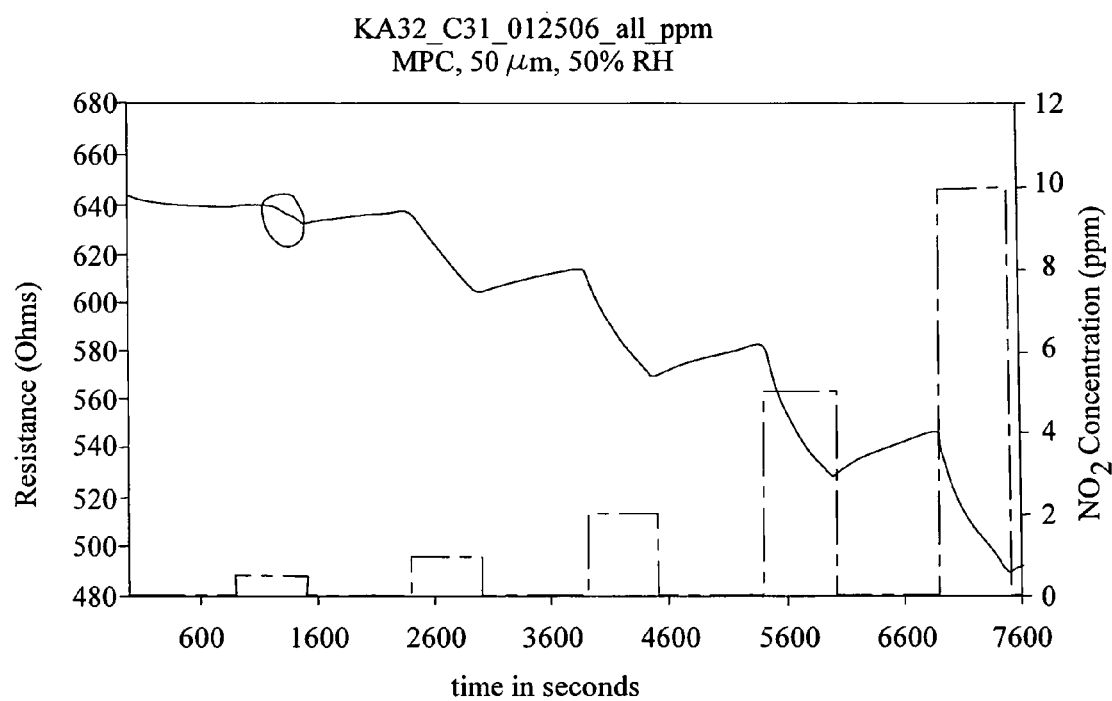
Figure 16D:
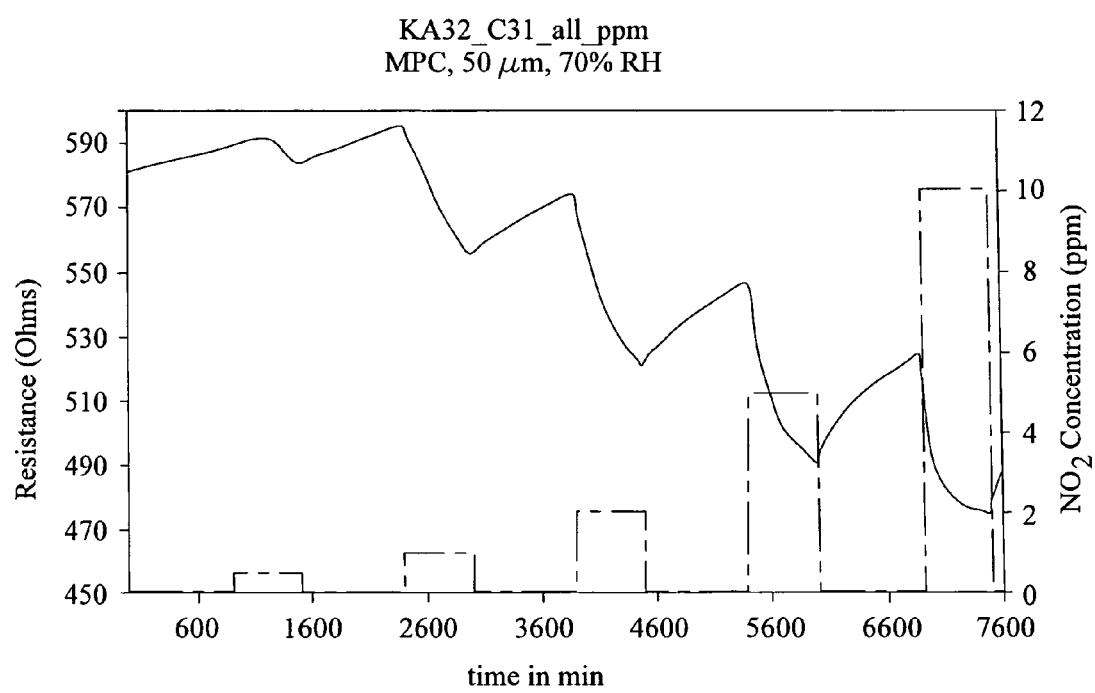
Figure 16E:
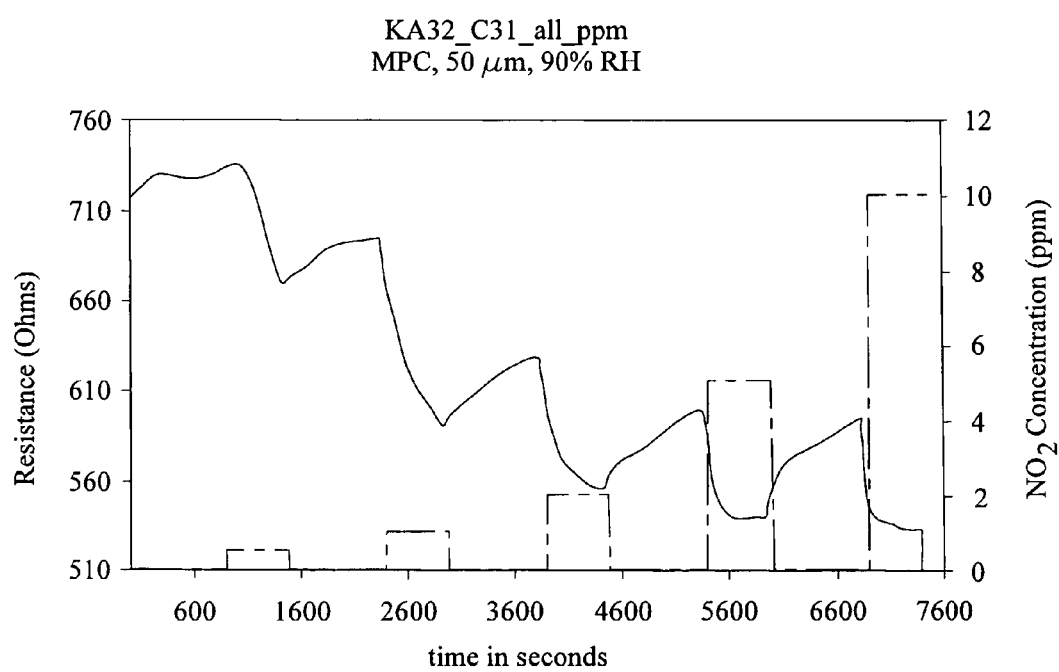
Figure 16F:
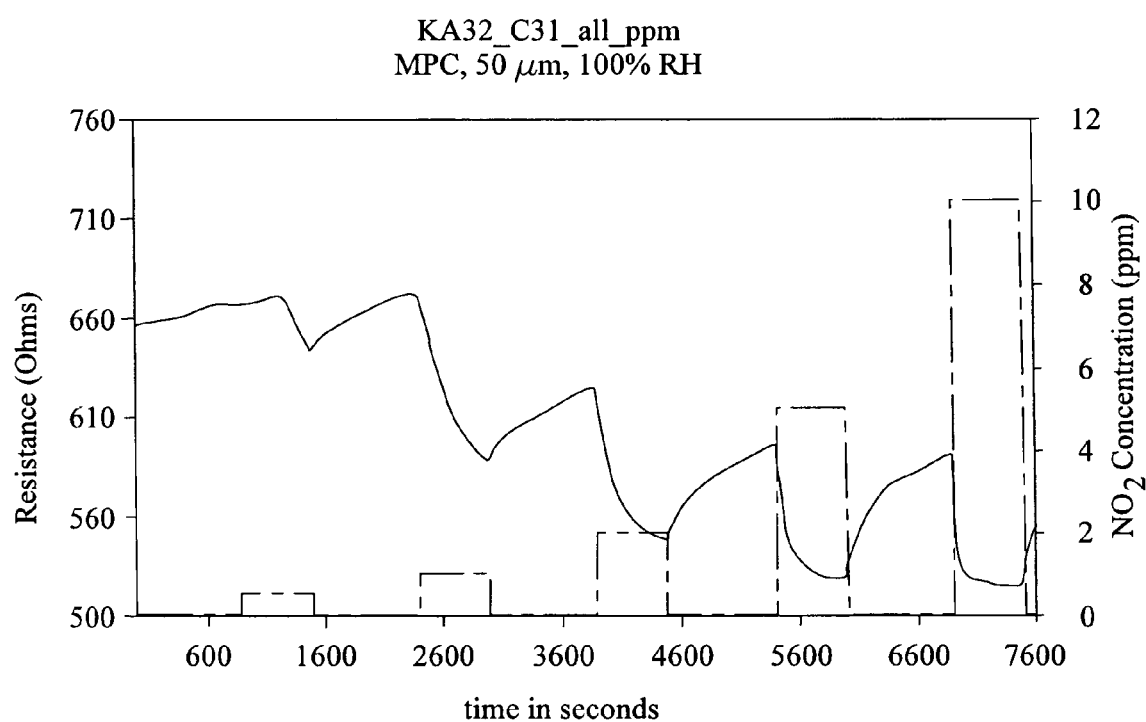

Introducing the dimensionless variable $$u = (RH/RH_0)_m, \quad (5)$$

several interesting values of u can be identified on FIG. 15: (1) a knee value, $u=w_{K1}$, where the first w-derivative is changing most rapidly; (2) a maximum slope value, $u=u_{MS}$, where the (negative) slope or u-derivative is a maximum value; and (2) a second knee value, $u=u_{K2}$ ($>u_m$), where the first u-derivative is again changing most rapidly. The values are estimated from the identities $$(\partial^2 F_e/\partial u^2)_{wK} = a \cdot \text{sech}^3 u \{\sinh^2 u - 1\}_K = 0, \quad (6A)$$

$$(\partial^3 F_e/\partial u^3)_{wMS} = a \cdot \text{sech}^4 u \{\cosh^2 u - 4\}_{MS} = 0, \quad (6B)$$

The value of the parameter a in the interval $0 < a \leq 1$ is irrelevant here. The solutions of Eqs. (6A) and (6B) are verified to be $$u_K = \sinh^{-1}\{1\} = \ln\{\sqrt{2} \pm 1\}, \quad (7A)$$

$$u_{K,MS} = \ln\{2 \pm \sqrt{3}\}, \quad (7B)$$

With appropriate choices of the parameter values $RH_0$ and m in Eq. (5), the experimentally observed locations of the values $u_{MS}$ and $u_{K1}$ can be matched.

An appropriate value of the parameter a can be determined as follows. Let $u = u_f$ correspond to the value of u for which $F_e(u_f) = f(0 < f < 1)$. From Eq. (3), this requires that $$a \cdot \text{sech}(u_f) + 1 - a = f, \quad (8A)$$

$$\text{sech}(u_f) = 1 - (1-f)/a), \quad (8B)$$

which requires that a lie in a reduced range, $1 - f < a \leq 1$. Equations (6A), (6B) and either (7A) or (7B) can be used to estimate $RH_0$, m and a.

If the approximation in Eq. (3) is adopted, the zero point relative response $V/V_0(RH=0)$ for a particular coating or dopant material can be compensated for the presence of moisture (RH>0) by a compensation factor such as $$V_0(RH=0) = V(RH>0)/\{a \cdot \text{sech}\{(RH/RH_0)^m\} + (1-a)\}. \quad (9)$$

Other approximations, replacing the sech(u) function in Eq. (3) by sec{u}, or by $\exp\{-u^2/u_0^2\}$, for example, can also be used here for compensation.

For a given coating or doping material and fixed temperature, the measured relative response V(RH;meas)/$V_0$, as relative humidity RH is increased over a sequence of values, can be compared with corresponding reference values V(RH;ref;h)/$V_0$ for each of a plurality of candidate gases (h=1, . . . , H) to determine if a particular candidate gas is present. Appendix C sets forth an analytical procedure for determining if a target gas is likely to be present, from a comparison of measured relative response values $V/V_0$ for a variable environmental parameter, such as relative humidity, temperature or pressure.

FIGS. 15-1, 15-2 and 15-3 illustrate sequences of measurements of a response parameter W (electrical resistance) for 3 IDEFs (12A-5, 12B-7, 12C-1) of the 32 coated or uncoated SWCNT sensors shown in FIG. 1, as a function of $NO_2$ gas concentration (2, 5 and 10 ppm), for varying relative humidity values of 0, 30, 50, 70 and 90 percent. The curves for RH=0 percent and RH=30 percent are substantially coincident in most, but not all, situations, which suggests that for RH no greater than a certain threshold (e.g., $RH_{thr} \approx 30$ percent), the response in change $\Delta W = (R/R0)-1$ is substantially the same as for RH=0 percent. For most, but not all, of the IDEFs in FIG. 1, the parameter change $\Delta W$ monotonically decreases as RH increases. For some of the IDEFs, the measured $\Delta W$ values do not vary in a simple manner with RH value at higher $NO_2$ concentration values.

FIGS. 16A, 16B, 16C, 16D, 16E and 16F graphically present time variation of the parameter W=electrical resistance for a coated SWCNT in the presence of $NO_2$ with time varying concentrations for relative humidity values RH=0, 0.3, 0.5, 0.7, 0.9 and 1.0, respectively. In each of FIGS. 16A-16F, the time varying $NO_2$ concentration $c(NO_2)$ follows a pattern set forth in Table 1

TABLE 1

| Time Variation of $NO_2$ Concentration. | |
|---|---|
| $0 \leq t < 800$ (sec) | $c(NO_2) = 0$ |
| $800 \leq t < 1500$ | $c(NO_2) = -0.5$ (ppm) |
| $1500 \leq t < 2400$ | $c(NO_2) = 0$ |
| $2400 \leq t < 3000$ | $c(NO_2) = 1$ |
| $3000 \leq t < 3900$ | $c(NO_2) = 0$ |
| $3900 \leq t < 4500$ | $c(NO_2) = 2$ |
| $4500 \leq t < 5300$ | $c(NO_2) = 0$ |
| $5300 \leq t < 6000$ | $c(NO_2) = 5$ |
| $6000 \leq t < 6900$ | $c(NO_2) = 0$ |
| $6900 \leq t < 7500$ | $c(NO_2) = 10$ |

In each of the graphs in FIGS. 16A-16F, the measured parameter value W=R/R0−1 manifests a decrease whenever a (new) non-zero value of $c(NO_2)$ is introduced, and the magnitude of this decrease increases monotonically with increasing time. However, for an intermediate time interval during which $c(NO_2)=0$ ppm, the measured parameter value W undergoes a monotonic partial recovery toward a higher W value. This recovery, as measured by the slope of the value G(t) for an intermediate time interval during which $c(NO_2)=0$ ppm, is mildest for RH=0, and this recovery slope increases in value approximately monotonically as the RH value increases.

For any one of the graphs in FIGS. 16A-16F, the temporal response of the W value in the different time intervals may be approximated as a sum of first order processes, $$W(t) = W1(t1)\exp\{-b1(RH, c(NO_2; 1))(t-t1)\} + W2(t1) \quad (10)$$
$$\{1 - \exp\{-b2(RH, c(NO_2; 1))(t-t1)\}(c(NO_2; 1) > 0, t \geq t1) =$$
$$W3(t2)\exp\{-b3(RH)(t-t2)\} +$$
$$W4(t2)\{1 - \exp\{-b4(RH)(t-t2)\}(c(NO_2) = 0, t \geq t2),$$

$$W2(t1)\{1 - \exp\{-b2(RH, c(NO_2; 1))(t2 - t1)\} = W3(t2), \quad (11)$$

where the $NO_2$ concentration is assumed to change from $c(NO_2)=0$ at t<t1 to $c(NO_2;1)>0$ at t=t1, and to change from $c(NO_2;1)=0$ to $c(NO_2)=0$ at t=t2 (>t1). The exponent coefficients b1, b2, b3 and b4 are monotonically increasing with increasing values of the relative humidity parameter RH. The coefficient value W1(t1) is the initial value of the parameter W at t=t1, when the concentration changes from $c(NO_2)=0$ to $c(NO_2)=c(NO_2;1)$; the coefficient W2(t1) is the asymptotic value of the parameter W, where the concentration $c(NO_2)=c(NO_2)$ is maintained indefinitely; and the coefficient W4(t2) is the asymptotic value of the parameter W where the concentration $c(NO_2)=0$ is maintained indefinitely.

The measured relative response $V/V_0$ or parameter value W may also drift with elapsed time $\Delta t$, measured relative to a time at which the coated or doped SWCNT sensor was initially prepared. If it is assumed here that the drift is a single first order process, the relative response, as a function of elapsed time $\Delta t = t - t_0$, may be approximated as $$V(\Delta t)/V(t_0) \approx b \cdot \exp\{(-\Delta t \Delta t_0)\} + (1-b), \quad (12)$$

where b is a non-zero value (positive or negative) and $\Delta t_0$ is a positive time increment. The quantity $\Delta t_0$ can be determined from the combination $$V(2\Delta t)/V(t_0) - V(\Delta t)/V(t_0) = \exp\{(-\Delta t/\Delta t_0)\}V(\Delta t)/V(t_0) - V(0)/V(t_0) \quad (13)$$

The quantity b is then estimated from a relation $$b \approx \{1 - V(\Delta t)/V(t_0)\}/\{1 - \exp\{(-\Delta t/\Delta t_0)\}\}. \quad (15)$$

Drift with elapsed time $\Delta t$ of the measured relative response value $V/V_0$ can then be compensated by computing a value $V(\Delta t_2)$ in terms of a value at another time $$V(\Delta t_2) = V(\Delta t_1) + b \exp\{(-\Delta t_2/\Delta t_0) - \exp\{(-\Delta t_1/\Delta t_0)\}\}, \quad (16)$$

$$V(t_0) \approx V(\Delta t)/\{b \cdot \exp\{(-\Delta t/\Delta t_0)\} + (1-b)\}, \quad (17)$$

where the quantities b and $\Delta t_0$ are assumed known with reasonable accuracy. The correctness of the representation in Eq. (12) can be evaluated by forming $$R(\Delta t) = \ln|V(2\Delta t)/V(t_0) - V(\Delta t)/V(t_0) - \ln|V(\Delta t)/V(t_0 - V(0)/V(t_0)|, \quad (18)$$

for two or more selected distinct positive values, $\Delta t = \Delta t1$ and $\Delta t = \Delta t2$. If the representation in Eq. (12) is substantially correct, the ratio identity $$R(\Delta t_1)/R(\Delta t_2) = \Delta t_1/\Delta t_2 \quad (19)$$

will be substantially satisfied for any distinct, positive values of $\Delta t_1$ and $\Delta t_2$.

*Where the temporal drift involves two or more different first order processes so that Eq. (19) is not substantially satisfied, for example, $$v(\Delta t) = V(\Delta t)/V(t_0) \approx b1 \exp\{(-\Delta t/\Delta t_{01})\} + b2 \exp\{(-\Delta t/\Delta t_{02})\}(1-b1-b2), \quad (20)$$

the computations are somewhat more complex. For simplicity, it is assumed that $\Delta t_{02} \gg \Delta t_{01}$ and that $\Delta t \geq \Delta t_{01}$ so that $$\exp\{(-\Delta t/\Delta t_{02})\} \gg \exp\{(-\Delta t/\Delta t_{01})\} \quad (21)$$

and $\exp\{(-\Delta t/\Delta t_{02})\}$ can be ignored relative to $\exp\{(-\Delta t/\Delta t_{01})\}$. This assumption should be verified a posteriori. One how forms the differences $$v(\Delta t) - v(0) \approx b1(x_1 - 1) + b2, \quad (22A)$$

$$v(2\Delta t) - v(\Delta t) \approx b1 \cdot x_1 (x_1 - 1), \quad (22B)$$

$$v(3\Delta t) - v(2\Delta t) \approx b1 \cdot x_1^2 (x_1 - 1) \quad (22C)$$

$$x_1 = \exp(-\Delta t/\Delta t_{01}), \quad (22D)$$

and the ratio $$R' = \{v(3\Delta t) - v(2\Delta t)\}/\{v(2\Delta t) - v(\Delta t)\} \quad (23)$$
$$= \{x_1^3 - x_1^2\}/\{x_1^2 - x_1\}.$$

Eq. (23) is a cubic polynomial in the unknown $x_1$ and can be factored into $$x_1(x_1 - 1)(x_1 - R') = 0 \quad (24)$$

for which the realistic solution is $$x_1 = R', \quad (25A)$$

$$\Delta t_{01} = \Delta t/\ln\{1/R'\}. \quad (25B)$$

From the preceding Eqs. (20A), (20B) and (23), one finds that $$b1 \approx \{v(2\Delta t) - v(\Delta t)\}/R'(R' - 1), \quad (26)$$

$$b2 = \{v(\Delta t) - v(0)\} - \{v(2\Delta t) - v(\Delta t)\}/R, \quad (27)$$

$$\Delta t_2 = -\Delta t/\{\ln\{v(\Delta t) - b1\exp(-\Delta t/\Delta t_{01}) + b1 + b2 - 1\} - \ln(b2)\}, \quad (28)$$

$$V(t_0) = V(\Delta t)/\{b1 \exp\{(-\Delta t/\Delta t_{01})\} + b2 \exp\{(-\Delta t/\Delta t_{02})\}(1 - b1 - b2)\}, \quad (29)$$

Recall that $v(0)$, $v(\Delta t)$, $v(2\Delta t)$ and $v(3\Delta t)$ are measured quantities.

Figure 17A:
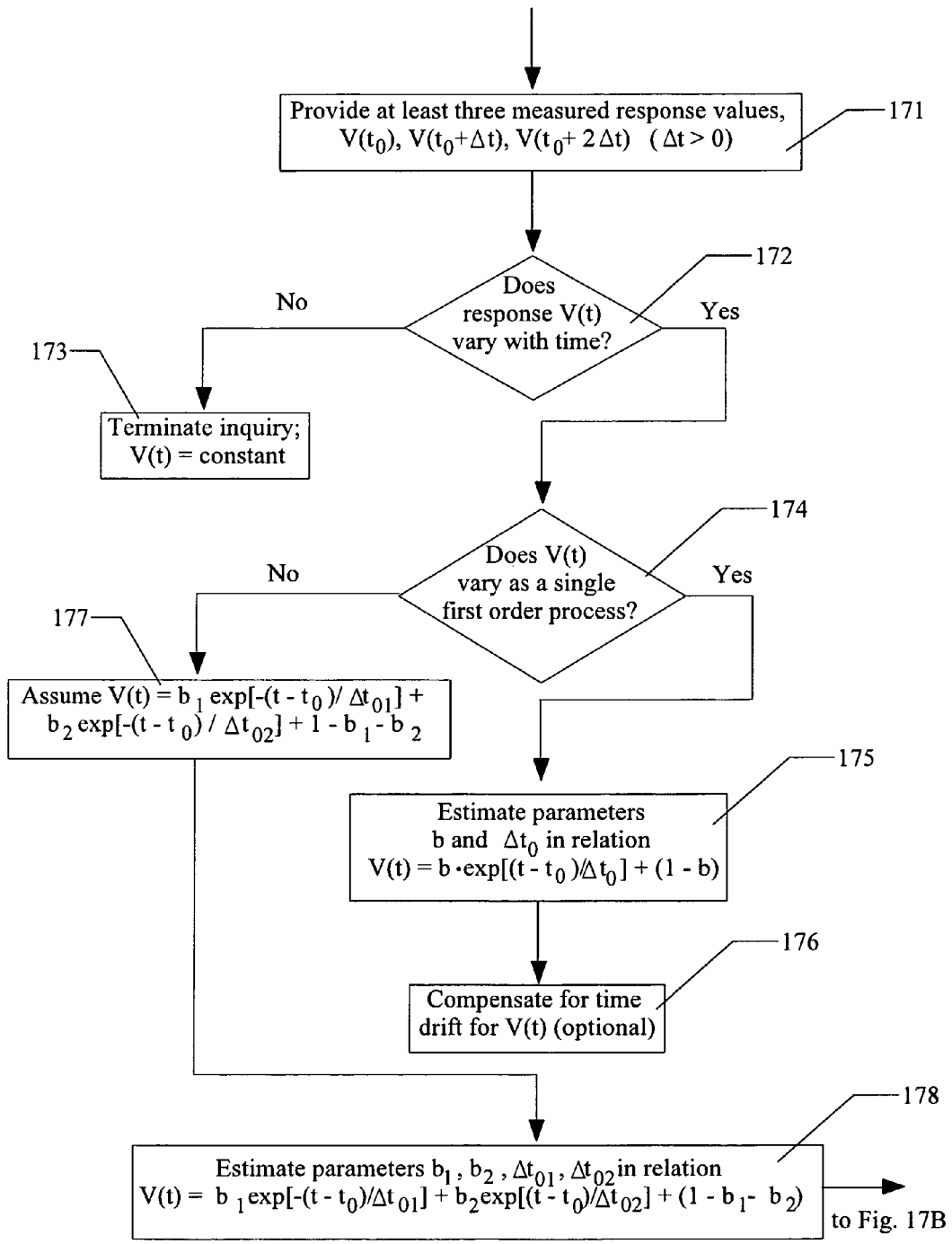
FIGS. 17 and 18 are flow charts of procedures for practicing the invention in the presence of temporal drift and for a selected environmental parameter.
Figure 17B:
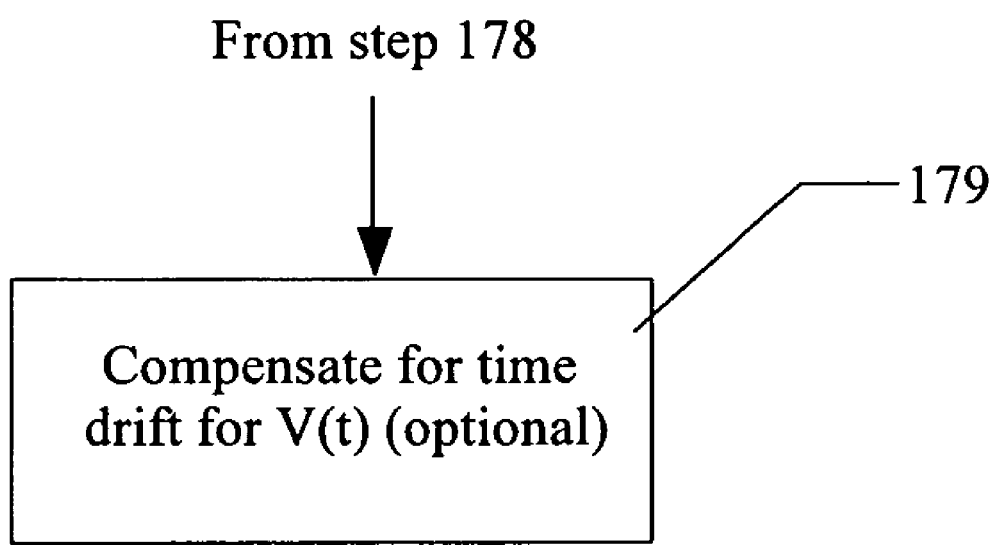

FIG. 17 is a flow chart of a procedure for analyzing or compensating for drift with elapsed time $\Delta t$ of a parameter value or relative response $V/V(t_0)$. In step 171, the system receives at least three measured response values, $V(t_0)$, $V(t_0 + \Delta t)$ and $V(t_0 + 2\Delta t)$, for a response, where $\Delta t > 0$. In step 172, the system determines if the response value varies with time, for example, by comparing two or more of the response values, measured at different times, $\Delta t_1$ and $\Delta t_2$. If the answer to the query in step 172 is "no," the system terminates the inquiry, in step 173, because the response value is substantially constant in time.

If the answer to the query in step 172 is "yes," the system determines if the response value $V(t)$ varies according to a single first order process, in step 174, for example, using the analysis developed in connection with Eqs. (12), (18) and (19), or another suitable analysis. If the answer to the query in step 174 is "yes" so that the relative response set forth in Eq. (12) is substantially correct, the system determines the parameters b and $\Delta t_0$, as developed in Eqs. (12)-(15), in step 175. The system optionally compensates for temporal drift, for this single first order process, for example, as indicated in Eq. (17)), in step 176.

If the answer to the query in step 174 is "no," the system optionally assumes that Eq. (20) is substantially correct, in step 177, where $\Delta t_{02} \ll \Delta t_{01}$ is assumed, and estimates the parameters b1, b2, $\Delta t_{01}$ and $\Delta t_{02}$, for example, as discussed in connection with Eqs. (20)-(28), in step 178. The system optionally compensates for temporal drift for this multiple first order process, for example, as indicated in Eq. (29), in step 179.

Appendix A. Estimation of Concentration of a Gas Component.

Figure 7:
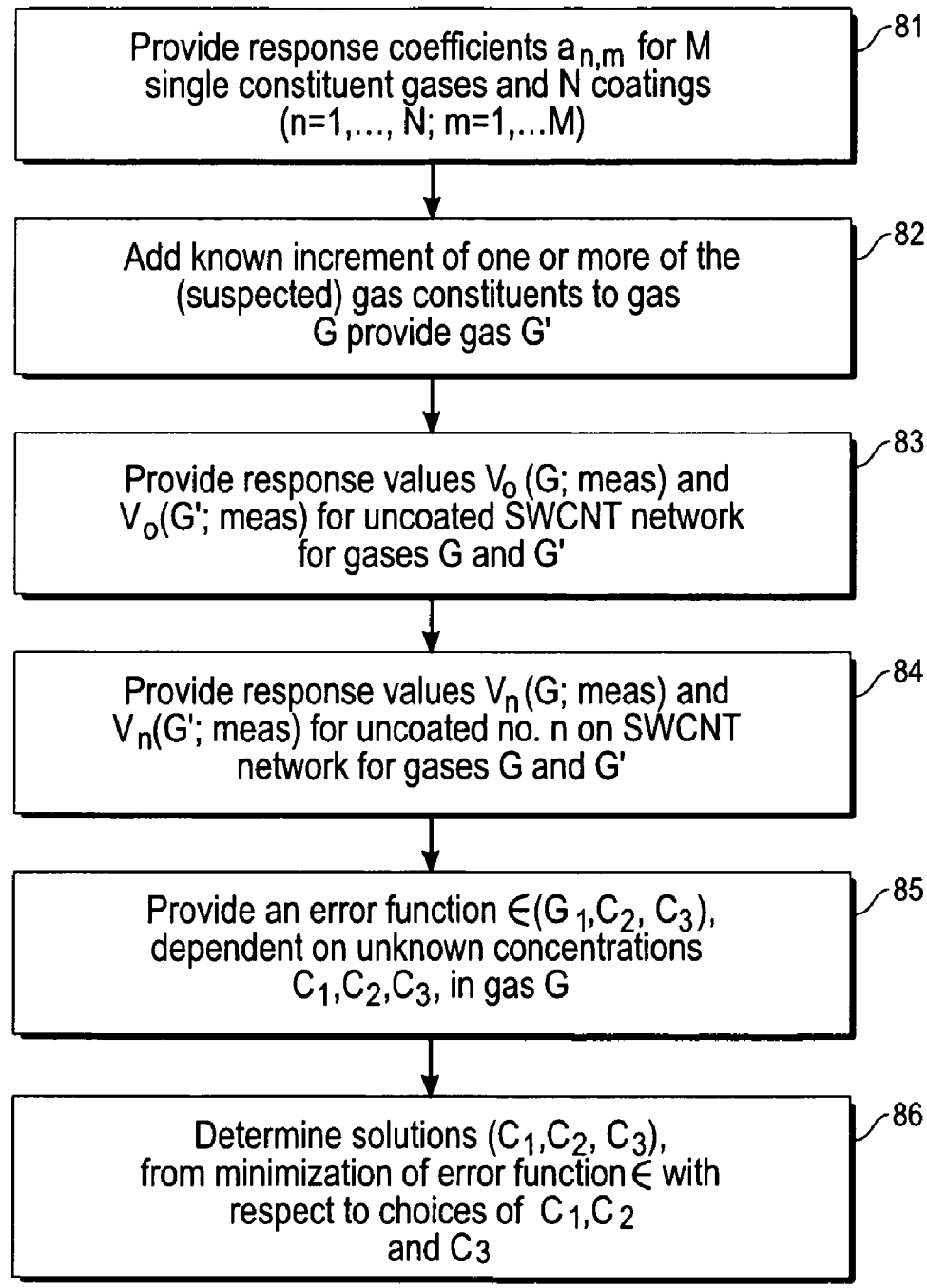
FIGS. 7 and 8 are flow charts of algorithms for estimation of concentrations of gas components and for determination of presence of a particular gas component, where a coated or doped SWCNT network is used.

FIG. 7 is a flow chart of a procedure for estimating concentration of a gas component that is suspected to be present. This approach requires knowledge of certain response coefficients relating change of a response value to increase or decrease in concentration of a particular gas component G. In step 81, response coefficients $a_{n,m}$ (n=1, ..., N; m=1, 2, ..., M) are estimated or otherwise provided for M single constituent gases (numbered m=1, ..., M; M≧) (such as $NO_2$, $Cl_2$ and HCl or for any other three gases of interest), in the presence of SWCNTs individually coated with each of N selected coatings (numbered n=1, ..., N; N≧1), for example, with chlorosulfonated polyethylene (n=1) and (separately) with hydroxypropyl cellulose (n=2).

For an SWCNT coated with coating number n, $$V_n(G;\text{meas}) - V_0(G;\text{meas}) = a_{n,1} \cdot c_{NO2} + a_{n,2} \cdot c_{Cl2} + a_{n,3} \cdot c_{HCl}, \quad (A1)$$

where, for example, $c_{NO2}$ represents the $NO_2$ concentration (e.g., expressed in ppm or in ppb). The set of response coefficients $\{a_{n,m}\}_m$ for different coatings, n=n1 and for n=n2 (≠n1), will differ from each other, but each set is determined or estimated by measurement of the response value difference, $V_n(G;\text{meas}) - V_0(G;\text{meas})$, of coated (n) versus uncoated (n=0), for each of the two (or, more generally, M≧2) single constituent gases present in a known concentration. For a single constituent gas $NO_2$ and no coating (n=0), for example, $a_{0,1} = 0.034 \pm 0.002$.

In step 82, a known increment of one (or more) of the (suspected) constituent (e.g., $NO_2$ or $Cl_2$ or HCl), is added to the gas unknown gas G to provide an augmented gas G'. In step 83, the response values, $V_0(G;\text{meas})$ and $V_0(G';\text{meas})$, for the uncoated SWCNT network (n=0), in the presence of the gases G and G', are measured or otherwise provided. In step 84, the response values, $V_n(G;\text{meas})$ and $V_n(G';\text{meas})$, for the SWCNT network coated with the (single) coating number n, in the presence of the gases G and G', respectively, are measured or otherwise provided.

In step 85, an error function $\epsilon$, defined by $$2\epsilon(x,y,z) = \Sigma_n w_n \cdot \{V_n(G;\text{meas}) - V_0(G;\text{meas}) - a_{n,1}c_1 - a_{n,2}c_2 + a_{n,3}c_3\}^2 + \Sigma_n w'_n \cdot \{V_n(G';\text{meas}) - V_0(G';\text{meas}) - a_{n,1}(c_1 + \Delta c_1) - a_{n,2}c_2 + a_{n,3}c_3\}^2, \quad (A2)$$

is provided, where $c_1$, $c_2$ and $c_3$ refer to the concentrations of the reference molecule, the first gas molecule and the second gas molecule, $\Delta c_1$ is a known concentration increment of a selected one ($c_1$) of the reference molecule, the first gas molecule or the second gas molecule, added to the gas G to provide the gas G', and $w_n$, and $w'_n$ are selected non-negative weight values. The two sums in Eq. (A2) represent the contributions of the initial composition and the augmented composition, respectively. These sums over n may include one, two, three or more coatings for which the response coefficients are known. In this example, n=1, 2.

The error function $\epsilon(c_1, c_2, c_3)$ is to be minimized with respect to choices of the (unknown) concentration values $c_1$, $c_2$ and $c_3$. Differentiating $\epsilon$ with respect to each of the variables $c_1$, $c_2$ and $c_3$, in step 86, one obtains three coupled linear equations in these variables:

$$\{(w_1 + w'_1)a_{1,1}^2 + (w_2 + w'_2)a_{2,1}^2\}c_1 + \quad (A3)$$
$$\{(w_1 + w'_1)a_{1,1}a_{1,2} + (w_2 + w'_2)a_{2,1}a_{2,2}\}c_2 + $$
$$\{(w_1 + w'_1)a_{1,1}a_{1,3} + (w_2 + w'_2)a_{2,1}a_{2,3}\}c_3 = $$
$$\{w_1(V_1(G;\text{meas}) - V_0(G;\text{meas})) + $$
$$w'_1(V_1(G';\text{meas}) - V_0(G';\text{meas})) - a_{1,1}\Delta c_1)\}$$
$$a_{1,1} + \{w_2(V_2(G;\text{meas}) - V_0(G;\text{meas})) + $$
$$w'_2(V_2(G';\text{meas}) - V_0(G';\text{meas})) - a_{2,1}\Delta c_1)\}a_{2,1},$$

$$\{(w_1 + w'_1)a_{1,1}a_{1,2} + (w_2 + w'_2)a_{2,1}a_{2,2}\}c_1 + \quad (A4)$$
$$\{(w_1 + w'_1)a_{1,2}^2 + (w_2 + w'_2)a_{2,2}^2\}c_2 + $$
$$\{(w_1 + w'_1)a_{1,3}a_{1,2} + (w_2 + w'_2)a_{2,3}a_{2,2}\}c_3 = $$
$$\{w_1 V_1(G;\text{meas}) + w'_1(V_1(G';\text{meas}) - a_{1,1}\Delta c_1)\}a_{1,2} + $$
$$\{w_2 V_2(G;\text{meas}) - V_0(G;\text{meas})) + $$
$$w'_2(V_2(G';\text{meas}) - V_0(G';\text{meas})) - a_{2,1}\Delta c_1)\}a_{2,2},$$

$$\{(w_1 + w'_1)a_{1,1}a_{1,3} + (w_2 + w'_2)a_{2,1}a_{2,3}\}c_1 + \quad (A5)$$
$$\{(w_1 + w'_1)a_{1,2}a_{1,3} + (w_2 + w'_2)a_{2,1}a_{2,2}\}c_2 + $$
$$\{(w_1 + w'_1)a_{1,3}^2 + (w_2 + w'_2)a_{2,3}^2\}c_3 = $$
$$\{w_1 V_1(G;\text{meas}) - V_0(G;\text{meas})) + $$
$$w'_1(V_1(G';\text{meas}) - V_0(G';\text{meas})) - a_{1,1}\Delta c_1)\}$$
$$a_{1,3} + \{w_2 V_2(G;\text{meas}) - V_0(G;\text{meas})) + $$
$$w'_2(V_2 G';\text{meas}) - $$
$$V_0(G';\text{meas})) - a_{2,1}\Delta c_1)\}a_{2,3}.$$

In step 86, Eqs. (A1)-(A5) in the unknowns $c_1$, $c_2$ and $c_3$ are determined, using standard matrix inversion techniques, after verification that a 3×3 (more generally, M×M) coefficient matrix for the vector $[c_1\ c_2\ c_3]^{tr}$ has a non-zero determinant. These solutions, $[c_1\ c_2\ c_3]^{tr}$, provide estimates of the concentration values of the corresponding chemicals in the gas G (or in the gas G') in step 66 of FIG. 6.

Preferably, at least two of the weight values in Eq. (A2) are positive (e.g., ($w_1$, $w_2$) or ($w'_1$, $w'_2$) or ($w_1$, $w'_2$) or ($w'_1$, $w_2$)), and the relative sizes of the non-zero weights reflect the relative importance of the response measurements. If, as is likely, the four response measurements are believed to be equally important, one can choose $w_1 = w_2 = w'_1 = w'_2 = 1$. One can ignore one or two of the four measurements, in which event the corresponding weight value(s) is set equal to 0.

The response coefficients $a_{n,m}$ used in Eqs. (1) and (2) are not necessarily positive. For example, the response coefficient $a_{ij}$ for the gas constituent $NO_2$ is positive for several of the SWCNT coatings used, while the response coefficient $a_{ij}$ for $NH_3$ is observed to be negative for at least one of these coatings (FIG. 4).

More generally, where M reference gas components (numbered m=1, ..., M1) and target gas components (numbered m=M1+1, ..., M1+M2=M) with unknown concentrations are believed to be present and N coatings (numbered n=1, ..., N), the error function $\epsilon$ (analogous to Eq. (A2)) is defined by $$2\epsilon(c_1, \ldots, c_M) = \Sigma_n w_n \cdot \{V_n(G;\text{meas}) - V_0(G;\text{meas}) - \Sigma_m a_{n,m}c_m\}^2 + \Sigma_n w'_n \cdot \{V_n(G';\text{meas}) - V_0(G';\text{meas}) - \Sigma_m a_{n,1}(c_m + \Delta c_m)\}^2, \quad (A6)$$

where one, or more then one, concentration value $c_m$ is augmented by a known amount $\Delta c_m$. The error function $\epsilon$ is minimized by differentiation with respect to each of the unknown concentration values $c_m$. This yields M coupled equations $$\Sigma_n w_n \cdot \{V_n(G;\text{meas}) - V_0(G;\text{meas}) - \Sigma_m a_{n,m}c_{m0}\}a_{n,m0} + \Sigma_n w'_n \cdot \{V_n(G';\text{meas}) - V_0(G';\text{meas}) - \Sigma_m a_{n,m}(c_{m0} + \Delta c_{m0})\}a_{n,m0} = 0, \quad (A7)$$

for index values m0=1, 2, ..., M. These can be restated in a matrix format as $$\Sigma_n (w_n + w'_n) \{\Sigma_m a_{n,m}c_{m0}\}a_{n,m0} = \Sigma_n w_n \cdot \{V_n(G;\text{meas}) - V_0(G;\text{meas})\} + \Sigma_n w'_n \cdot \{\Sigma_m a_{n,m}\Delta c_{m0}\}a_{n,m0}, + \Sigma_n w'_n \cdot \{V_n(G';\text{meas}) - V_0(G';\text{meas})\}. \quad (A8)$$

After verifying that the determinant of the M×M matrix of coefficients for the quantities $c_{mo}$ in Eq. (A8) is non-zero, this M×M matrix can be inverted to determine estimates for the concentration values $c_{m0}$ (m0=1, ..., M). These concentration value estimates will depend, in part, upon the relative values chosen for the weight values $w_n$ and $w'_n$ for the coatings. Where one or more of the reference molecule concentration values $c_{m0}$ (m0=1, ..., M1) are known in advance, the estimates for these reference concentration values can be compared with the corresponding known values to evaluate the likely accuracy of the remaining estimated values.

The approach set forth in this Appendix A can also be used to estimate an initial concentration value $c_{m0}$ where the CNT network is doped or otherwise loaded, rather than being coated.

Appendix B. Determination of Bound on Gas Component Concentration.

A second algorithm does not require provision of a large number of response coefficients $a_{ij}$ but only seeks to determine if a particular target molecule is present in at least a selected concentration. For a selected coating, such as chlorosulfonated polyethylene or hydroxypropyl cellulose, on the CNT, a measurement of the response value difference $\Delta V = V$(coated)$-V$(uncoated) is taken for modified gases, G'(1) and G'(2), where each of two distinct supplemental concentration values, $\Delta_1 c(m0)$ and $\Delta_2 c(m0)$, respectively, for a selected molecule no. m0 (e.g., $NO_x$ or $Cl_2$ or HCl) is added to the original gas G. The concentration value $c_0(m0)$ of the selected molecule present in the original gas G is unknown, and the configuration of the CNT network is unknown. It is assumed that the response value difference $\Delta V$ increases approximately linearly with the concentration difference $\Delta c(m0)$ of the selected molecule so that $$\Delta V_1(m0) = v_0 + v_1 \cdot (c_0(m0) + \Delta_1 c(m0)), \quad (B1)$$

$$\Delta V_2(m0) = v_0 + v_1 \cdot (c_0(m0) + \Delta_2 c(m0)). \quad (B2)$$

A molecule m0 should be chosen for which $|\Delta_2 c(m0) - \Delta_1 c(m0)|$ is at least equal to a selected positive threshold. The quantities $v_0$, $v_1$ and $c_0(m0)$ are then related by the equations $$v_1 = (\Delta V_2(m0) - \Delta V_1(m0))/\{\Delta_2 c(m0) - \Delta_1 c(m0)\}, \quad (B3)$$

$$v_0 + v_1 \cdot c_0(m0) = \Delta V_1(m0) - v_1 \cdot \Delta_1 c(m0) \quad (B4)$$
$$= \Delta V_2(m0) - v_1 \cdot \Delta_2 c(m0),$$

and $v_0$ and $v_1$ are determined, in part, by the CNT network configuration (assumed fixed and reusable) that is present. Where, as is likely, $v_0 \geq 0$, one infers that the initial concentration value $c_0(m0)$ for the molecule m0 is limited by $$c_0(m0) = \{\Delta V_1(m0) - v0\}/v_1 - \Delta_1 c(m0) \leq \{\Delta V_1(m0)/v_1\} - \Delta_1 c(m0) \quad (B5\text{-}1)$$

or $$c_0(m0) = \{\Delta V_2(m0) - v0\}/v_1 - \Delta_2 c(m0) \leq \{\Delta V_2(m0)/v_1\} - \Delta_2 c(m0) \quad (B5\text{-}2)$$

Equations (B5-1) and (B5-2) provide[[s]] an upper bound for the quantity $c_0(m0)$. Where it is known that the coefficient $v_0$ is non-positive, Eqs._(B5-1) and (B5-2) can be inverted to provide lower bounds for the concentration:

$$c_0(m0) = \{\Delta V_1(m0) - v0\}/v_1 - \Delta_1 c(m0) \geq \{\Delta V_1(m0)/v_1\} - \Delta_1 c(m0) \quad (B6\text{-}1)$$

or $$c_0(m0) = \{\Delta V_2(m0) - v0\}/v_1 - \Delta_2 c(m0) \geq \{\Delta V_2(m0)/v_1\} - \Delta_2 c(m0) \quad (B6\text{-}2)$$

This approach does not provide a direct estimate for the quantity $C_0(m0)$, only an indication of whether the molecule m0 is or is not present in a concentration of no more than the right hand quantity in Eqs. (B5-1) or (B5-2). However, this approach does not require determination and use of the response coefficients $a_{ij}$ that are required for the putatively more accurate method set forth in Appendix A. The method of Appendix B can be used to estimate upper (or lower) bounds for concentration values C of one, two or more selected molecules.

FIG. 8 is a flow chart of a procedure for estimating an upper bound for a concentration value $c_0(m0)$ for a selected molecule in the gas G. It is assumed that the response value difference $\Delta V$ varies approximately linearly with the concentration difference $\Delta c(m0)$ of the selected molecule. In step 91, first and second (distinct) known increments, $\Delta_1 c(m0)$ and $\Delta_2 c(m0)$, of a selected molecule m0 are added to a gas G to provide first and second augmented gases, G1 and G2. In step 92, response value differences, $$\Delta V_1(m0)) = V(G1;\text{meas}) - V(G;\text{meas}), \quad (B7)$$

$$\Delta V_2(m0)) = V(G2;\text{meas}) - V(G;\text{meas}), \quad (B8)$$

are measured or otherwise provided. In step 93, the coefficient v1 in an approximation for response value differences $$\Delta V_1(m0) = v_0 + v_1 \cdot \{c_0(m0) + \Delta_1 c(m0)\}, \quad (B9)$$

$$\Delta V_2(m0) = v_0 + v_1 \cdot \{c_0(m0) + \Delta_2 c(m0)\}, \quad (B10)$$

is determined according to $$v_1 = (\Delta V_2(m0) - \Delta V_1(m0))/\{\Delta_2 c(m0) - \Delta_1 c(m0)\}. \quad (B11)$$

In step 94, the system queries whether the coefficient $v_0$ is likely non-negative. If the answer to the query in step 94 is "yes," the system estimates an upper bound for the initial concentration value $c_0(m0)$, in step 95:

$$c_0(m0) \leq \{\Delta V_1(m0)/v_1 - \Delta_1 c(m0) = \Delta V_2(m0)/v_1 - \Delta_2 c(m0) \quad (v_0 \geq 0). \quad (B12)$$

If the answer to the query in step 94 is "no," the system estimates a lower bound for the initial concentration value $c_0(m0)$, in step 96:

$$c_0(m0) \geq \{\Delta V_1(m0)/v_1 - \Delta_1 c(m0) = \Delta V_2(m0)/v_1 - \Delta_2 c(m0) \quad (v_0 \geq 0). \quad (B13)$$

Appendix C. Effect of Varying Environmental Parameter.

Figure 18:
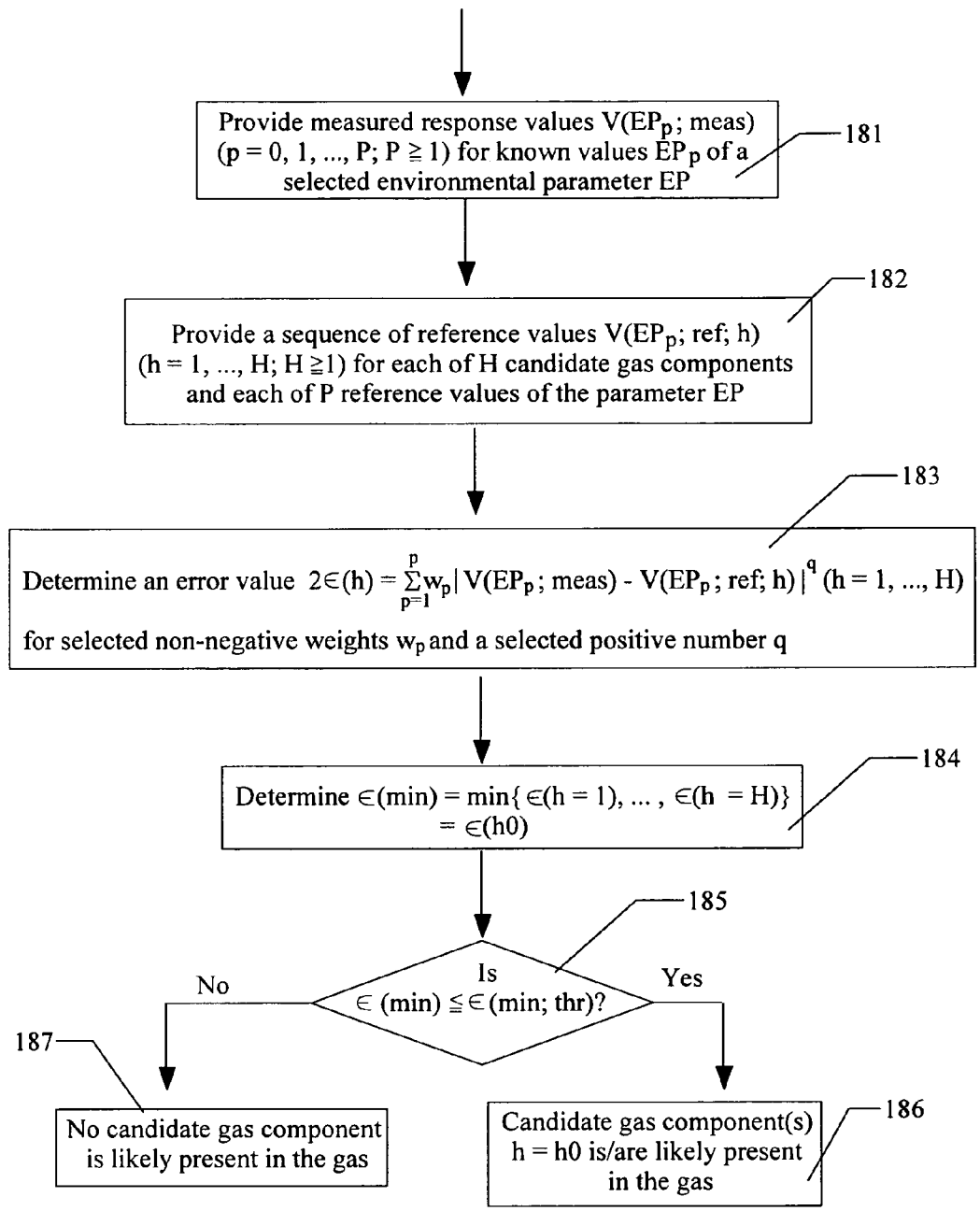

FIG. 18 is a flow chart of a procedure for estimating concentration of a candidate gas component, suspected to be present in a target gas, where a response parameter V is associated with a controllably varied environmental parameter ("EP"), and measurements of the response V(G;meas) are available for a sequence of reference values of EP, $\{EP_p\}_p$. The environmental parameter(s) EP may be one or more of the following: relative humidity RH, temperature T, gauge pressure GP, ambient chemicals present AC, and elapsed time $\Delta t$ since the test sample was prepared.

In step 181, measurements of the response $V(EP_p;\text{meas})$ ($p = 0, 1, \ldots, P; P \geq 1$) are provided, where $p = 0$ may correspond to EP equal to a reference value, such as RH=0 or 0.1, for example. In step 182, a sequence of reference values $V(EP_p; \text{ref}; h)$ ($h = 1, \ldots, H: H \geq 1$) is provided, for each of H candidate gas components and for each of P reference values of the environmental parameter EP. In step 183, the system determines an error value $$2\varepsilon(h) = \left\{ \sum_{p=1}^{P} w_p |V(EP_p; \text{meas}) - V(EP_p; \text{ref}; h)|^q \right\} (h = 1, \ldots, H), \quad (C1)$$

where $w_p$ is a non-negative weight associated with the environmental parameter value $EP_p$ and q is a selected positive number (e.g., q=1 or 2). If desired, the approximation $F_e((EP/EP_0)^m;a)$ in Eq. (3) may be substituted for the reference quantity $V(EP_p;\text{ref};h)$.

In steps 184 and 185, a minimum error value (or values)

$$\varepsilon(\min) = \min\{\varepsilon(h=1), \ldots, \varepsilon(h=H)\} \quad (C2)$$

is/are determined (e.g., $\varepsilon(\min) = \varepsilon(h=h0)$), and $\varepsilon(\min)$ is compared with a selected threshold value $\varepsilon(\min;\text{thr})$. If $$\varepsilon(\min) = \varepsilon(h=h0) \leq \varepsilon(\min;\text{thr}), \quad (C3)$$

the system interprets these conditions as indicating that the candidate gas component(s) corresponding to h=h0 is/are likely present in the target gas, in step 186. If the condition (C3) is not satisfied, the system interprets this result as indicating that none of the gas component(s) h0 is likely to be present in the target gas, in step 187.

What is claimed is:

1. A method of sensing presence or absence of a specified gas molecule in a target gas, the method comprising:
providing, in a chamber, a target gas that may contain up to H candidate gas molecules present with unknown concentrations $c_h$, numbered $h = 1, \ldots, H$ ($H \geq 1$), first and second interdigitated electrodes, connected to at least one of (i) a voltage source having a controllable voltage difference and (ii) a controllable current source, and a path Q that includes a plurality of carbon nanotubes (CNTs) and that extends between the first and second interdigitated electrodes, where the path Q is loaded with at least one loading chemical and is exposed to the target gas;

providing, within the chamber, an environment having a sequence of values $EP_p$ (p=1, ..., P;P≥1) of at least one environmental parameter, chosen from among temperature, relative humidity, pH and gauge pressure;

measuring, between the first and second interdigitated electrodes, in a presence of the target gas, an electrical parameter value ("response value"), denoted $V(EP_p; \{c_h\};meas)$, of at least one of electrical current, electrical conductance, voltage difference and electrical resistance, where the target gas experiences an environment having at least one of the environmental parameter values $EP_p$;

providing reference response values $V(\{EP_p\};\{c_h(\text{ref})\};\text{ref})$ for a sequence of reference values of known concentrations, $\{c_h(\text{ref})\}=\{c_{h=1}(\text{ref}),\ldots,c_{h=H}(\text{ref})\}$, for the path Q exposed to an environment having the environmental parameter value or values $\{EP_p\}$;

approximating the sequence of electrical parameter values $V(\{EP_p\}; \{c_h(\text{ref})\};\text{ref})$ as linear combinations, $$\approx V(EP_p;\{c_h\};\text{approx})=a_0+a_1c_1+\ldots+a_Hc_H, \approx V(EP_p;\{c_h(\text{ref})\};\text{ref})$$

of the concentration values $c_h$ of the candidate gas molecules, where $a_0, \ldots, a_H$ are known response coefficients that may depend upon one or more values $EP_p$ of at least one of the environmental parameters that the candidate gas molecules experience, and $a_0$ represents a response coefficient when none of the candidate gas molecules is present;

estimating an error value $\epsilon(\{c_h\})$ for the candidate gas molecule concentrations $c_h$, the error value being expressed as $$\varepsilon(\{c_h\}) = \sum_{h=1}^{H}\sum_{p=1}^{P} w_p|V(\{EP_p\}; \{c_h\}; \text{approx}) - V(\{EP_p\}; \{c_h\}; \text{meas})|^q,$$

where $w_p$ is a non-negative weight value that may vary with estimated relative importance of the environmental parameter values $EP_p$ and q is a positive number;

determining or providing concentration values $c_h=c_h(\text{min})$ (h=1, ..., H) in the approximate response values $V(\{EP_p\}; \{c_h\};\text{approx})$ that provide a minimum error value, $\epsilon(\{c_h\};\text{min})=\epsilon(\{c_h=c_h(\text{min})\})$, for the error value $\epsilon(\{c_h\})$;

comparing the minimum error value $\epsilon(\{c_h\};\text{min})$ with a positive threshold error value $\epsilon(\text{min.thr})$;

when $\epsilon(\{c_h\};\text{min})\leq\epsilon(\text{min;thr})$, interpreting this condition as indicating that at least one of the H candidate gas molecules, designated as h=h0, is present in the target gas, and that the concentration value of at least one candidate gas molecule that is present in the target gas is substantially equal to $c_{h=h0}(\text{min})$; and when $\epsilon(c_h;\text{min})>\epsilon(\text{min;thr})$ for all h=1, ..., H, interpreting this condition as indicating that none of the H candidate gas molecules is likely to be present in the target gas.

2. The method of claim 1, further comprising
choosing said exponent q equal to 2;
partially differentiating said error value $\epsilon(\{c_h\})$ with respect to each of said concentration values $c_h$ (h=1, ..., H) and setting each of the resulting partial derivative equations equal to 0, to obtain a system of non-homogeneous equations in said concentration values $c_h$;
obtaining solutions, $c_h=c_h(\text{sol})$, of the system of non-homogeneous equations; and
interpreting at least one of the solutions $c_h(\text{sol})$ as said value $c_{h=h0}(\text{min})$ that would provide a minimum value for said error value $\epsilon(\{c_h\})$.

3. The method of claim 1, further comprising choosing said weight values $w_p$ to have substantially identical, positive values.

4. The method of claim 1, further comprising choosing said candidate gas molecule from a group consisting of $NO_x$, $NH_3$, acetone, benzene, nitrotoluene, $F_2$, $Cl_2$, $Br_2$, $I_2$, HF, HCl, HBr, HI, FCl, FBr, FI, ClBr, ClI, BrI, an alcohol, an aldehyde and a ketone.

5. The method of claim 4, further comprising:
drawing said loading chemical from the group of loading chemicals consisting of chlorosulfonated polyethylene, hydroxypropyl cellulose, polystyrene and polyvinylalcohol; and
providing said loading chemical by at least one of (i) coating at least one of said plurality of said CNTs in said path Q with said loading chemical, and (ii) doping at least one of said plurality of said CNTs in said path Q. with said loading chemical.

6. The method of claim 1, further comprising choosing said candidate gas molecule from a group consisting of at least one hydrocarbon and at least one oxide of carbon.

7. The method of claim 6, further comprising:
drawing said loading chemical from the group of loading chemicals consisting of Pd, Pt, Rh, Ir, Ru, Os and Au; and
providing said loading chemical by at least one of (i) coating said loading chemical on said at least one of said plurality of said CNTs in said path Q, and (ii) doping at least one of said plurality of said CNTs in said path Q. with said loading chemical.

8. The method of claim 1, further comprising:
exposing at least one of said plurality of said CNTs in said path Q to light having an ultraviolet component for a time interval having at least a specified time interval length $\Delta t(\text{min})$; and
allowing at least one of said candidate gas molecules of said target gas to become desorbed from at least one of said plurality of said CNTs in said path Q.

9. The method of claim 1, further comprising including on at least one of said first and second interdigitated electrodes a coating of at least one of Ti and Au, having a thickness in a specified range, deposited on an exposed surface of a substrate that is substantially nonconducting electrically.

10. The method of claim 1, further comprising choosing said CNTs to include at least one single wall carbon nanotube.

* * * * *